(12) United States Patent
Sibbett

(10) Patent No.: US 6,749,733 B1
(45) Date of Patent: Jun. 15, 2004

(54) MATERIALS CLASSIFIER, METHOD OF USING, AND METHOD OF MAKING

(75) Inventor: Scott S. Sibbett, Corrales, NM (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/547,049

(22) Filed: Apr. 10, 2000

(51) Int. Cl.[7] .................... G01N 27/447; G01N 27/453; G01N 30/02
(52) U.S. Cl. ...................... 204/450; 204/460; 204/606; 204/600; 210/656; 422/70
(58) Field of Search ................................. 204/643, 644, 204/616, 606, 610, 600, 466, 450, 547, 548, 554, 660; 422/70; 210/656

(56) References Cited

U.S. PATENT DOCUMENTS

| | | | | |
|---|---|---|---|---|
| 4,315,812 A | * | 2/1982 | Karlson ...................... | 204/647 |
| 4,440,638 A | * | 4/1984 | Judy et al. .................. | 204/672 |
| 5,180,480 A | * | 1/1993 | Manz .......................... | 204/644 |
| 5,565,077 A | * | 10/1996 | Gold et al. .................. | 204/666 |
| 5,582,773 A | * | 12/1996 | Cass ....................... | 252/519.12 |
| 5,990,041 A | * | 11/1999 | Chung et al. ................ | 502/416 |

OTHER PUBLICATIONS

E. Boncinelli, et al., An Agarose Gel Resolving a Wide Range of DNA Fragment Lengths, Analytical Bichemestry, Oct., 1983, pps. 40–43.
W. A. Gobie, C. F. Ivory, Recycle Continuous–Flow Electrophoresis: Zero–Difusion Theory, AICheE Journal, Mar. 1988, pps. 474–482.
H. A. Pohl, Dielectrophoresis (The behavior of neutral matter in nonuniform electric fields), Cambridge University Press, 1978, Only Table of Contents provided.
N. Burggraf, et al., Synchronized Cyclic Capillary Electrophoresis– A Novel Approach to Ion Separations in Solution, Journal of High Resolution Chromatography, 10/93, pps. 594–596.
E. M. Southern, A Preparative Gel Electrophoresis Apparatus for Large Scale Separations, Analaytical Biochemistry, Jul. 2, 1979, pps. 304–318.
C.F. Chou, et al., Continuous Sorting of DNA in a Microfabricated Array, Meeting of The American Physical Society, Session WC31, Mar. 1999.
S.H. Zaidi, et al., Interferometric Lithography Exposure Tool for 180–nm Structures, Proceedings of SPIE, Mar. 10–11, 1997, pps. 248–254.
P. Mattock, et al., Velocity Gradient Stablished, Continuous, Free Flow Electrophoresis. A Review, Separation and Purification Methods, Marcel Dekker, Inc. 1980, pps. 1–69.
A. Manz, et al., Planar Chips Technology for Miniaturization and Integration of Separation Techniques into Monitoring Systems, Journal of Chromatography, 1992, pps. 253–257.
P.M. Rolchigo, D.J. Graves, Analytical and Preparative Electrophoresis in a Nonuniform Electric Field, AIChE Journal, Mar. 1988, pps. 483–492.
L. B. Koutny, et al., Michrochip Electrophoretic Immunoassay for Serum Cortisol, Analytical Chemistry, Jan. 1, 1996, pps. 18–22.

(List continued on next page.)

*Primary Examiner*—Alex Noguerola
(74) *Attorney, Agent, or Firm*—Blakely, Sokoloff, Taylor & Zafman LLP

(57) ABSTRACT

The present invention relates to a method of classifying charged molecules such as proteins for quantitative analysis. An analyte solution of the molecules is subjected to separational forces may be fluid drag and electrophoretic force in opposition. The analyte solution may be subjected to a two-phase process. The two-phase process may add both electrophoretic force based upon molecule charge, and differential mobility resistance based upon molecule mass and/or size.

35 Claims, 20 Drawing Sheets

OTHER PUBLICATIONS

A. T. Woolley, R. A. Mathies, Ultra–High–Speed DNA Sequencing Using Capillary Electrophoresis Chips, Analytical Chemistry, Oct. 15, 1995, pps. 3676–3680.

C.S. Effenhauser, et al., High–Speed Separation of Antisense Oligonucleotides on a Micromachined Capillary Electrophoresis Device, Anal. Chem., Sep. 15, 1994, pps. 2949–2953.

C.S. Effenhauser, et al., Glass Chips for High–Speed Capillary Electrophoresis Separations with Submicrometer Plate Heights, Analytical Chemistry, Oct. 1, 1993, pps. 2637–2642.

T.F. Hooker, et al., High Performance Capillary Electorphoresis, Chapter 17 (Two–Dimensional Separations in High–Performance Capillary Electrophoresis), John Wiley & Sons, Inc. 1998.

A.T. Woolley, R.A. Mathies, Ultra–high–speed DNA fragment separations using microfabricated capillary array electrophoresis chips, Proc. Natl. Acad. Sci. USA, 11/94, pps. 11348–11352.

S. Turner, H. G. Craighead, DNA Motioin in Nanofabricated Artifcial Gels, Meeting of The American Physical Society, Session WC31, Mar. 1999.

T.A.J. Duke, R.H. Austin, Micro fabricated Sieve for the Continuous Sorting of Macromolecules, Phys. Review Letters, The American Phys. Soc., Feb. 16, 1998, pps. 1552–1555.

Bill Steele, Nanofabricated artifical gels could replace cumbersome organic polymers to speed DNA sequencing,Cornell University News, www.news.cornell.edu/releases, Mar. 25, 1999.

D.J. Harrison, et al., Capillary Electrophoresis and Sample Injection Systems Integrated on a Planar Glass Chip, Analytical Chemistry, Sep. 1992, pps. 1926–1932.

D.E. Raymond, et al., Continuous Sample Pretreatment Using a Free–Flow Electrophoresis Device Integrated onto a Silicon Chip, Analytical Chemistry, Sep. 15, 1994, pps. 2858–2865.

D.C. Schwartz, C.R. Cantor, Separation of Yeast Chromosome–Sized DNAs by Pulsed Field Gradient Gel Electrophoresis, Cell, MIT, May 1984, pps. 67–75.

W. S. Koegler, C. F. Ivory, Field Gradient Focusing: A Novel Method for Protein Separation, Biotechnol. Prog. 1996, vol. 12, No. 6, pps. 822–836.

Z. Huang, C.F. Ivory, Digitally Controlled Electroporetic Focusing, Analytical Chemistry, Apr. 15, 1999, pps. 1628–1632.

J. Khandurina, et al., Microfabricated Porous Membrane Structure for Sample Concentration and Electrophoretic Analysis, Analytical Chemistry, May 1, 1999, pps. 1815–1819.

S.C. Jacobson, et al., High–Speed Separations on a Microchip, Analytical Chemistry, Apr. 1, 1994, pps. 1114–1118.

S.C. Jacobson, et al., Microchip Structures for Submillisecond Electrophoresis, Analytical Chemistry, Aug. 15, 1998, pp. 3476–3480.

Rainer Barbieri et al., "Enhanced hybridization labeling signals in Southern blotted DNAs fractionated with voltage gradient gel electrophoresis," *Electrophoresis* 1998, 19, 643–645.

Vincenzo Izzo et al., "Multiple voltage–gradient gel electrophoresis system," *Electrophoresis* 2001, 22, 29–32.

Asaro, M.R. et al., "Modified apparatus for voltage gradient gel electrophoresis," *Journal of Chromatography A.* 855 (1999) 723–726.

Rainer Barbieri et al., "Voltage Gradient Electrophoresis of Nucleic Acids on Agarose Gels," *Analytical Biochemistry* 212, 168–172 (1993).

Pflug W., "Wedge–shaped ultrathin plyacrylamide and agarose gels for isoelectric focusing: A new method for typing phosphoglucomutase ($PGM_1$) in semen stains and vaginal swabs," *Electrophoresis* 1985, 6, 19–22.

Dennison, C. et al., "Nonuniform Field Gel Electrophoreses," *Analytical Biochemistry* 120, 12–18, (1982).

Boncinelli, E. et al., "An Agarose Gel Resolving a Wide Range of DNA Fragment Lengths," *Analytical Biochemistry* 134, 40–43 (1983).

* cited by examiner

MATERIALS CLASSIFIER, METHOD OF USING, AND METHOD OF MAKING

BACKGROUND OF THE INVENTION

1. Field of the Invention

The present invention relates generally to micro electro-mechanical structure (MEMS) fabrication, and, more specifically, the present invention relates to the fabrication of a MEMS classifier for charged molecules. In particular, the present invention relates to a classifier for protein molecules that may bear opposite charges and that may have unequal masses.

2. Description of Related Art

One current primary method for separation of charged molecules in solution such as proteins is 2-dimensional polyacrylamide gel electrophoresis (PAGE). This method requires a laborious multi-step preparation of unstable gels, followed by extensive manual working of the gels by skilled technicians. Quantification of the separated molecules is performed typically by visual or photographic inspection of the resulting gels.

A second common method for separation of charged molecules in solution is matrix assisted laser desorption ionization (MALDI) mass spectrometry. This method does not require gels or gel manipulation to separate and quantify a mixture of charged molecules. However, it requires sophisticated vacuum chamber technology, and therefore is too cumbersome for use anywhere but a dedicated lab environment, and requires an expensive hardware investment.

Another technique uses micro fabricated structures. Capillary electrophoresis synchronized cyclic electrophoresis, free-flow electrophoresis, and capillary gel electrophoresis have been demonstrated to separate ions. None of these techniques have the resolving power of 2-dimensional PAGE, and therefore are incapable of separating and quantifying mixtures of many hundreds of different molecules. This general finding corroborates theoretical treatments on the inherent advantage of 2-dimensional chromatography to generate high total peak capacity. High total peak capacity is a measure of the theoretical maximum number of components that can be resolved, or differentiated, by the classifier within a given run.

What is needed is a classifier and method for separating charged molecules that overcomes the problems of the prior art.

BRIEF SUMMARY OF THE INVENTION

The present application also discloses a method of classifying a plurality of substances. In one embodiment, the method comprises providing a solid state classifier comprising a porous medium disposed between at least two electrodes, classifying a plurality of substances by differential mobility chromatography in the porous medium, and classifying the plurality of substances by electrophoresis, wherein the plurality of substances is classified along a plurality of positions within the solid state classifier by fixing charged molecules in place along at least one of the at least two electrodes.

BRIEF DESCRIPTION OF THE DRAWINGS

In order that the manner in which the above recited and other advantages of the invention are obtained, a more particular description of the invention briefly described above will be rendered by reference to specific embodiments thereof which are illustrated in the appended drawings. Understanding that these drawings depict only typical embodiments of the invention that are not necessarily drawn to scale and are not therefore to be considered to be limiting of its scope, the invention will be described and explained with additional specificity and detail through the use of the accompanying drawings in which.

DETAILED DESCRIPTION OF THE INVENTION

The present invention relates to the introduction of 2-dimensional porous media to a 1-dimensional capillary electrophoresis system. By this invention, charged molecules such as protein molecules can be separated and quantified for analysis. The present invention is advantageous because it eliminates the need for preparation of gels, eliminates gel instability, eliminates manual working of gels, and enables automated quantification of the charged molecules. Accordingly, the present invention provides a solid state charged molecule classifier and a method of fabricating it.

The inventive classifier described herein may be manufactured at various scales. However, it has been designed with conventional silicon process technology in mind such as complementary metal oxide silicon (CMOS) technology. The present invention is particularly advantageous at micro electromechanical structure (MEMS) scale. Many features of the inventive charged molecule classifier may be incorporated from standard components of MEMS technology, for example, microfluidic channels, electrodes, and capacitative detectors.

The following description includes terms, such as upper, lower, first, second, etc. that are used for descriptive purposes only and are not to be construed as limiting. The embodiments of an apparatus or article of the present invention described herein can be manufactured, used, or shipped in a number of positions and orientations. The term "substrate" generally refers to the physical object that is the basic workpiece that is transformed by various process operations into the desired article. A substrate may also be referred to as a wafer. Wafers may be made of semiconducting, non-semiconducting, or combinations of semiconducting and non-semiconducting materials.

Reference will now be made to the drawings wherein like structures will be provided with like reference designations. In order to show the structures of the present invention most clearly, the drawings included herein are diagrammatic representations of inventive articles. Thus, the actual appearance of the fabricated structures, for example in a photomicrograph, may appear different while still incorporating the essential structures of the present invention. Moreover, the drawings show only the structures necessary to understand the present invention. Additional structures known in the art have not been included to maintain the clarity of the drawings.

Figure 1:
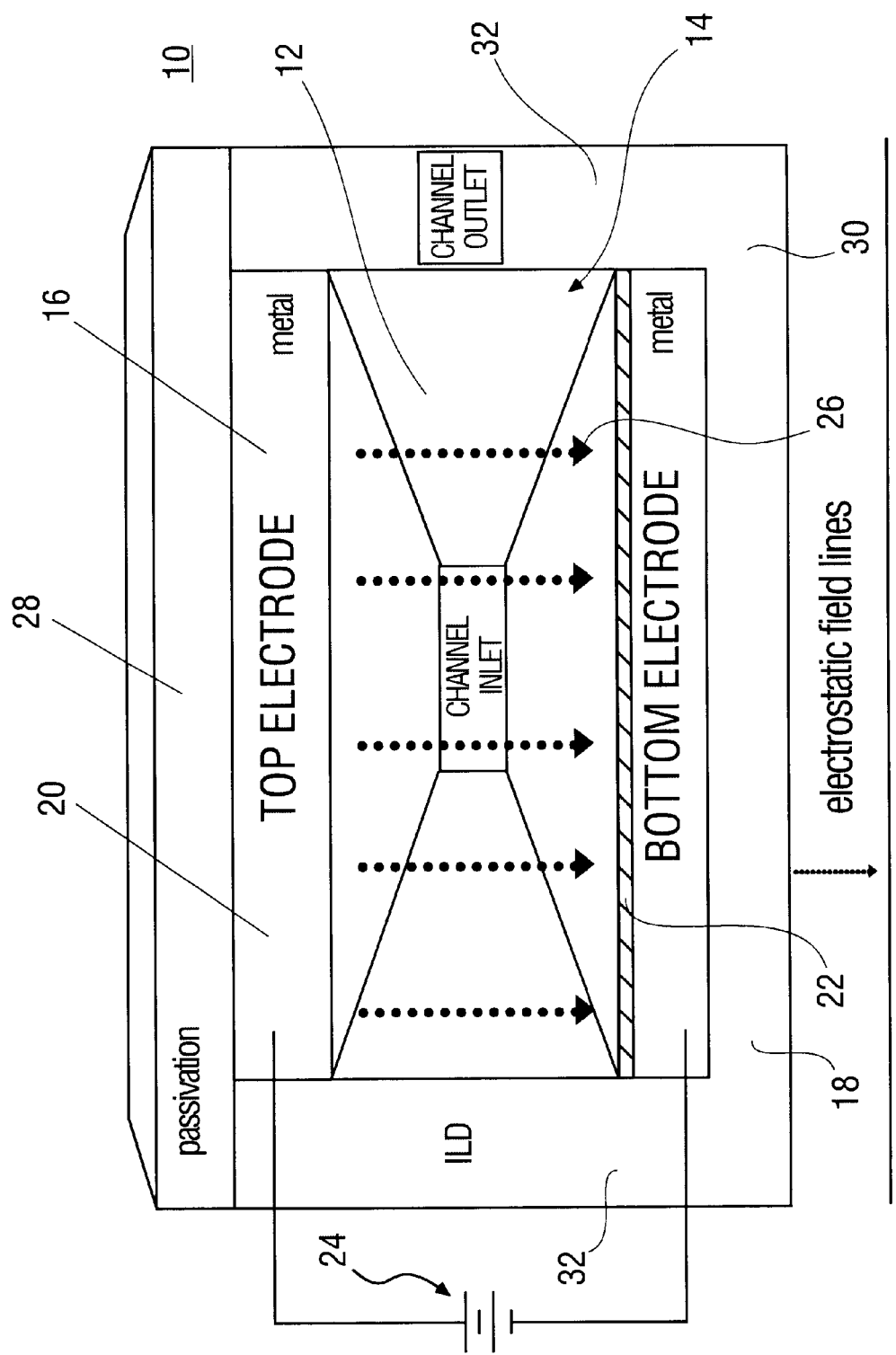
FIG. 1 depicts the view down the center axis of such a MEMS channel.

FIG. 1 illustrates rectangular channel 10 that is created with a channel inlet 12 and a channel outlet 14 at opposite sides. Additionally, a top electrode 16 and a bottom electrode 18 are respectively situated on the top wall 20 and bottom wall 22 of channel 10. FIG. 1 depicts the view down the center axis of channel 10. An electric field is established within channel 10 by a power source 24 that is connected between top electrode 16 and bottom electrode 18, as depicted by the electrophoretic field arrows 26 in FIG. 1. A top passivation layer 28 and a bottom passivation layer 30 may be provided both to protect respective top and bottom electrodes 16, 18 and to act as electrical insulators.

The side walls 32 of channel 10 including top wall 20 and bottom wall 22, are manufactured to be impermeable to liquids such as water and/or organic fluids or mixtures or emulsions thereof. The inventive method of forming a classifier, may include providing a dielectric first layer such as bottom wall 22. Next, a bottom electrode 18 is formed on the dielectric first layer comprising bottom wall 22. Thereafter, a channel 10 is formed by a second dielectric layer that may comprise sidewalls 34 of channel. A filter medium 36 is formed in channel 10 as set forth above. A top electrode 16 is formed above filter medium 36. Additionally, a third dielectric layer that may include passivation layer 28 is formed over the top electrode 16. Where a MEMS classifier is formed, the classifier is a solid sate device. Channel 10 may have a characteristic width, between sidewalls 32 from about 100 micrometers to about 1,000 micrometers, preferably about 500 micrometers.

Figure 2:
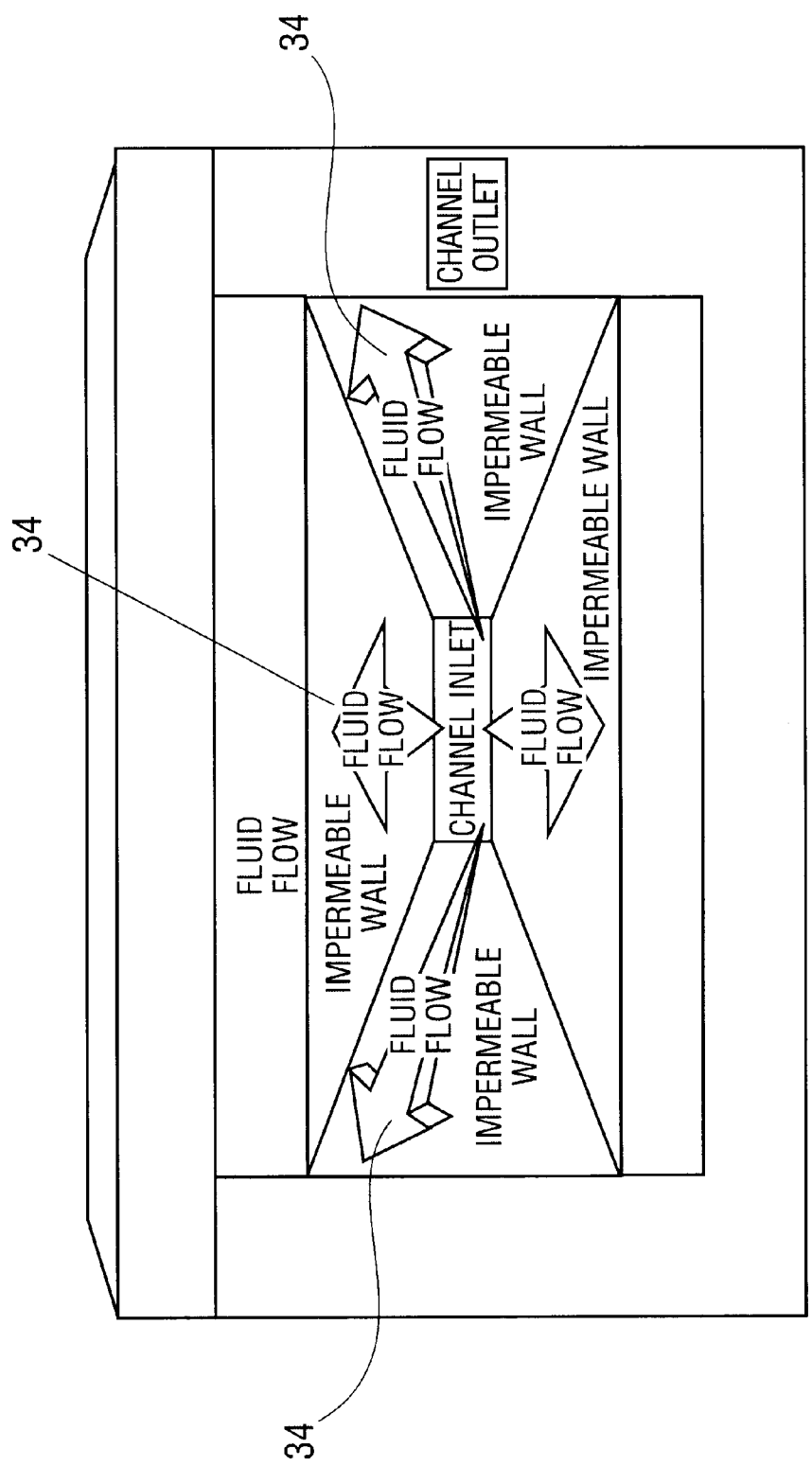
FIG. 2 illustrates how fluid is forced to flow into the inlet side of the channel, and to exit at the outlet side.

A pump (not pictured) causes fluid to flow into channel inlet 12, and to exit at channel outlet 14 as illustrated in FIG. 2 by fluid flow directional arrows 34. In addition to or alternative to the formation of directional fluid flow, sound waves may be imposed on molecules. Sound waves may replace or augment fluid flow as a driving force along one direction, and thereby eliminate or lessen the need for a pump.

Figure 3:
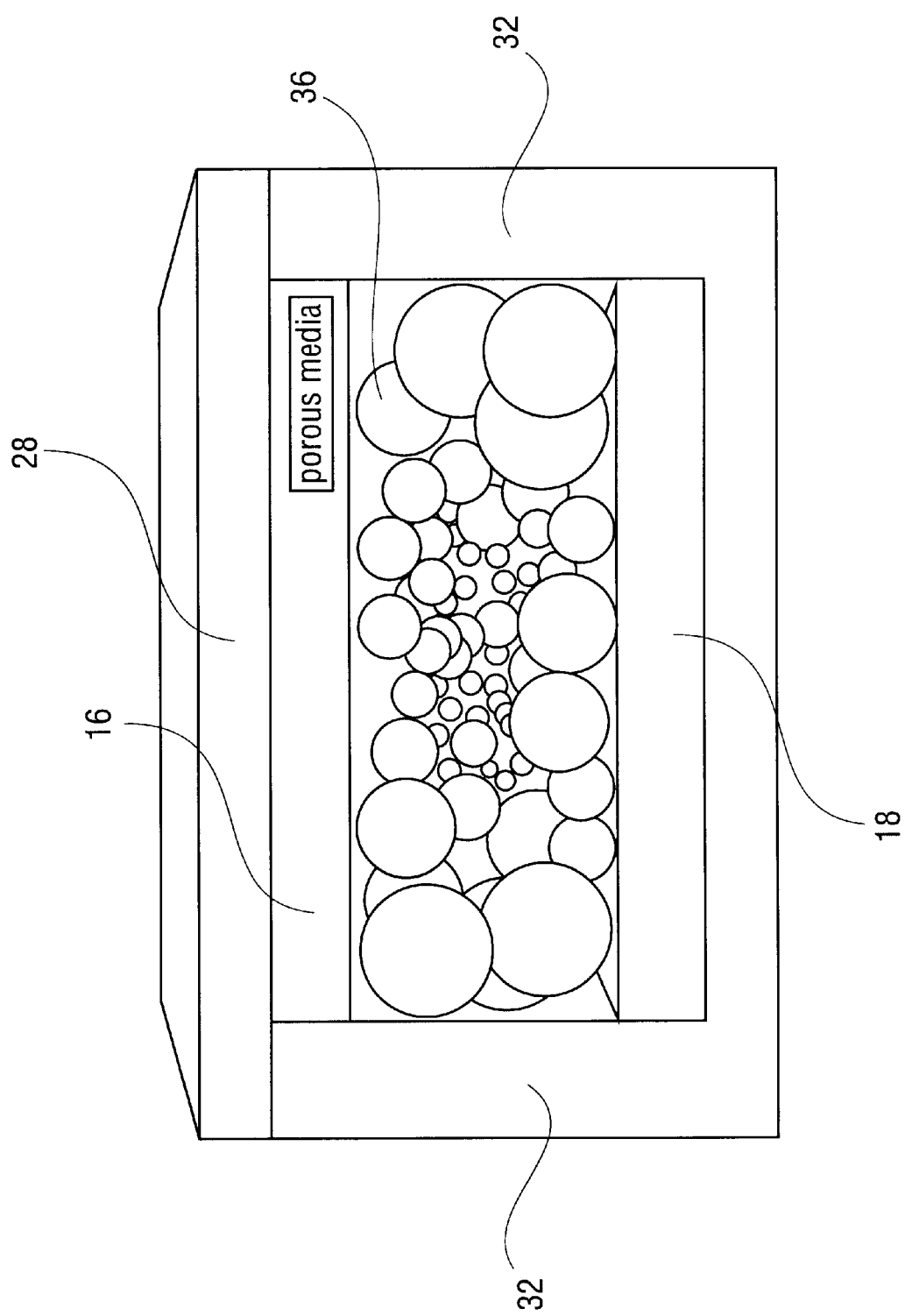
FIG. 3 illustrates the channel filled with a porous medium, such as porous silicon.

As illustrated in FIG. 3, channel 10 is filled with a porous medium 36, such as porous silicon, which exhibits conventional chromatographic properties, such as size exclusion. By means of backpressure, channel 10 may be caused to fill completely with liquid, resulting in substantial immersion of porous medium 36. Hence, porous medium 36 is used herein as a filter medium.

Channel 10 may be filled with an appropriately porous medium 36 depending upon a specific application. There are at least three methods for filling channel 10 with porous medium 36. A first method for filling channel 10 is by conventional damascene methods, involving bulk deposition such as chemical vapor deposition (CVD) of porous media 36 into a pre-defined trench that will become channel 10, followed by chemical-mechanical polishing (CMP), followed by bulk deposition of a capping layer such as top electrode 16 or a top wall 20 that may border channel 10 on one side and top electrode 16 on the other side.

A second method for filling channel 10 is by in situ processing of bulk films. For example, utilizing lithographic patterning to expose surface regions for example, regions of silicon or silicon oxide. These exposed regions may be chemically modified by standard methods such as by wet etching, plasma etching etc., to create, for example, porous silicon or sintered tantalum.

A third method for filling channel 10 with porous medium 36 is by physical pumping of liquid solutions of porous media such as beads or uncured gels into channel 10.

The invention described herein can be built by monolithic processing, such as conventional polysilicon surface micromachining. Therefore, the separations performed according to the present invention will be substantially cheaper at high-volume because of the economies of scale of monolithic processing versus non-monolithic processing.

Properties of porous medium 36 may be configured to match the molecular weights and shapes of the molecules to be separated. For instance, if protein molecules are to be separated, the average pore size of porous medium 36 may be manufactured in a range from about 50 Angstrom to about 100 Angstrom. Preferably the size is about 75 Angstrom, which is the average pore size of the polyacrylamide gel used in conventional electrophoresis of high-molecular weight molecules, such as proteins. CMOS-compatible materials with pores of this average size include treated silicon structures such as porous silicon and the like. Other CMOS-compatible materials with pores of this average size include metals and metal compounds such as, sintered tantalum powder, sintered niobium powder, sintered tungsten powder, sintered gamma titanium aluminide, and the like. Other CMOS-compatible materials with pores of this average size include micro machined structures such as silicon lattices.

Porous medium 36 poses a torturous path to solute molecules, and thereby causes solute molecules to be separated on differential mobilities due to differences of at least one of mass, charge, shape and the like. Porous medium 36 may have the added benefit of diminishing diffusional losses from a concentrated band that may form within channel 10 as is discussed below by providing a physical diffusion resistance.

Figure 4:
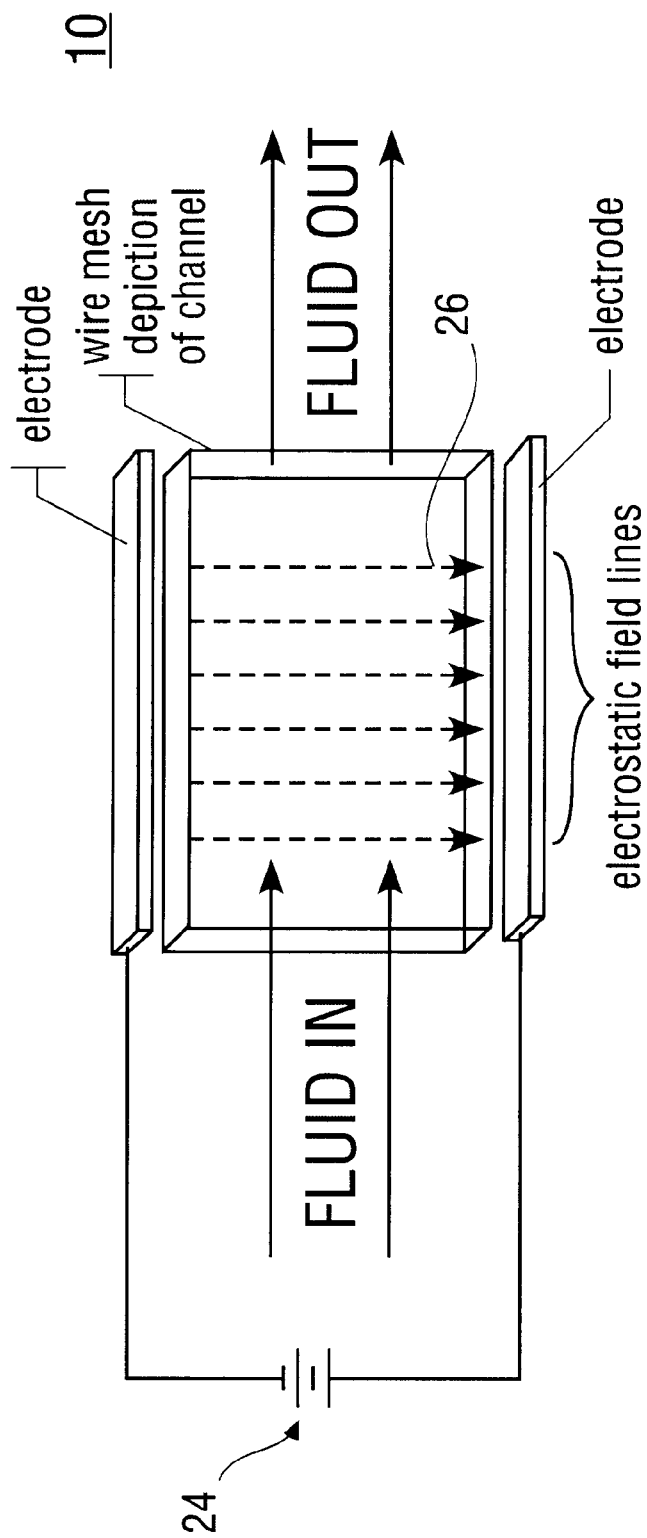
FIG. 4 illustrates an elevational cut-away view of the channel that depicts the two forces acting upon charged molecules in the channel: electrophoresis due to the electric field, and fluid drag due to fluid flow.

An elevational cut-away view of channel 10 is shown in FIG. 4. Two forces are depicted that act upon charged molecules in channel 10. The first force is electrophoresis due to directional electrostatic field lines depicted by directional electrophoretic arrows 26. The second force is differential mobility chromatography (DMC). DMC is accomplished by fluid drag due to viscous fluid flow that is opposed by the various pore sizes of porous medium 36 (not pictured).

Figure 5:
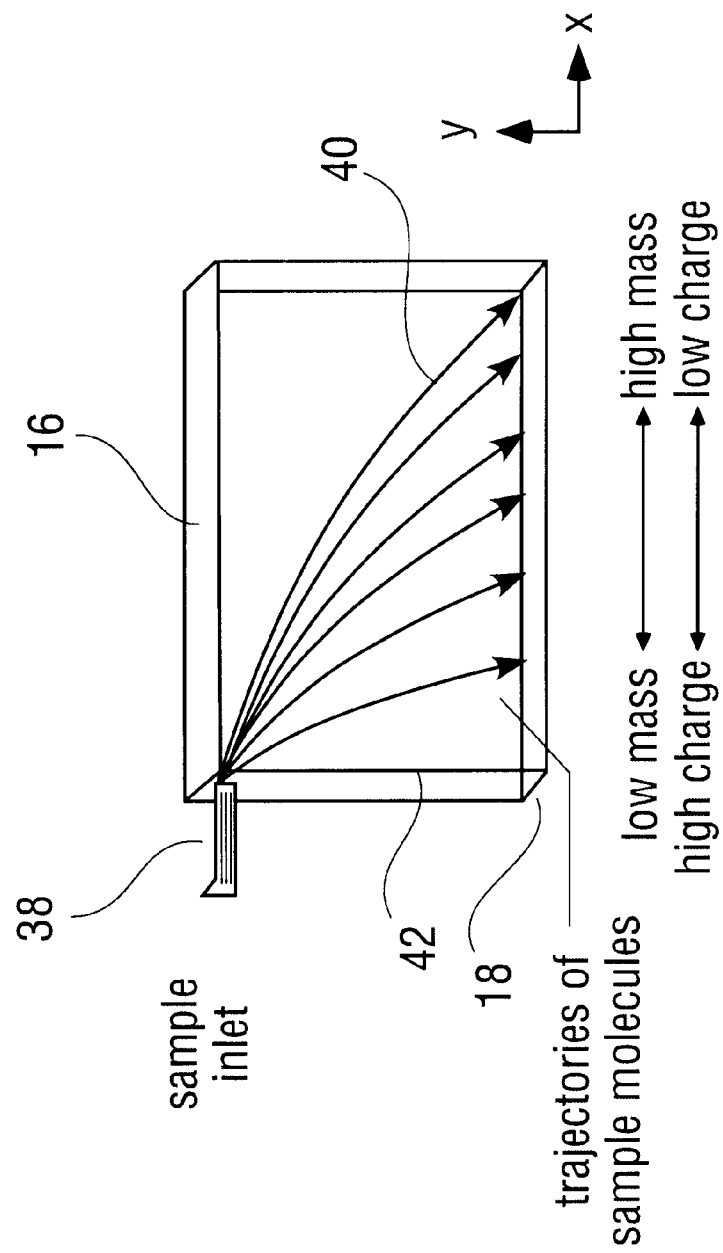
FIG. 5 illustrates a mixture of charged molecules in solution that is introduced into the fluid flow at or near a point of an electric field gradient.

A mixture of charged molecules in solution is introduced into the fluid flow at or near a sample inlet region 38 of an effective electric field as illustrated in FIG. 5. According to this embodiment, at least three processing schemes may be employed to accommodate three different charge states of molecules that are to be classified and quantitatively analyzed. A first processing scheme exists where all molecules to be classified are net negative in charge. The molecules in the mixture will classify based on at least the on of the properties of charge, mass, and shape of individual molecules. Referring to FIG. 5, molecules of negative charge tend to be swept electrophoretically away from top electrode 16 toward bottom electrode 18, in the negative y direction.

FIG. 5 illustrates the situation where pore size of porous medium 36 tends to entrain molecules of smaller mass. In this situation, for molecules of higher mass and low charge, fluid drag forces will tend to dominate over eletrophoretic forces. Hence, the trajectory 40 of the higher mass molecules will tend to be longer than the trajectory 42 for lower mass molecules before they collide at or near bottom electrode 18 of channel 10. Thereupon, the molecules are fixed in place by the applied directional electrophoretic field 26, and by molecular forces, such as van der Waal's forces.

On the other hand, for molecules of low mass and high charge, the electrophoretic force will dominate over fluid drag, therefore the trajectory 42 for lower mass molecules will tend to be shorter. Eventually, all charged molecules in the injected sample may collide with the impermeable bottom wall 22 adjacent to bottom electrode 18 depending upon specific engineering of dimensions and overall characteristics of channel 10.

FIG. 5 illustrates a situation where smaller mass molecules may tend to become entrained in micro fissures in the porous medium. The smaller molecules are therefore drawn through the inventive classifier at a slower rate than larger molecules that tend to be too large to become entrained in the micro fissures in the porous medium.

In a second processing scheme, all molecules to be classified are net positive in charge. This situation is exactly the opposite of the first processing scheme. Molecules of positive charge tend to be swept electrophoretically from bottom to top, in the positive y direction. Hence, the molecules are almost immediately swept toward upper electrode 16; little or no classification is achieved. To remedy this, the polarity of directional eletrophoretic field 26 is reversed, and the classifier will classify the sample of positive molecules similar to the first processing scheme. It should be noted that since the inventive classification method may be carried out in 1-G, gravitational forces may have an effect upon classification. However, where molecule size and fluid viscosity are typically going to cause the molecules to behave in the Stokes flow regime, gravitational effects may have no consequence upon classification.

Figure 6:
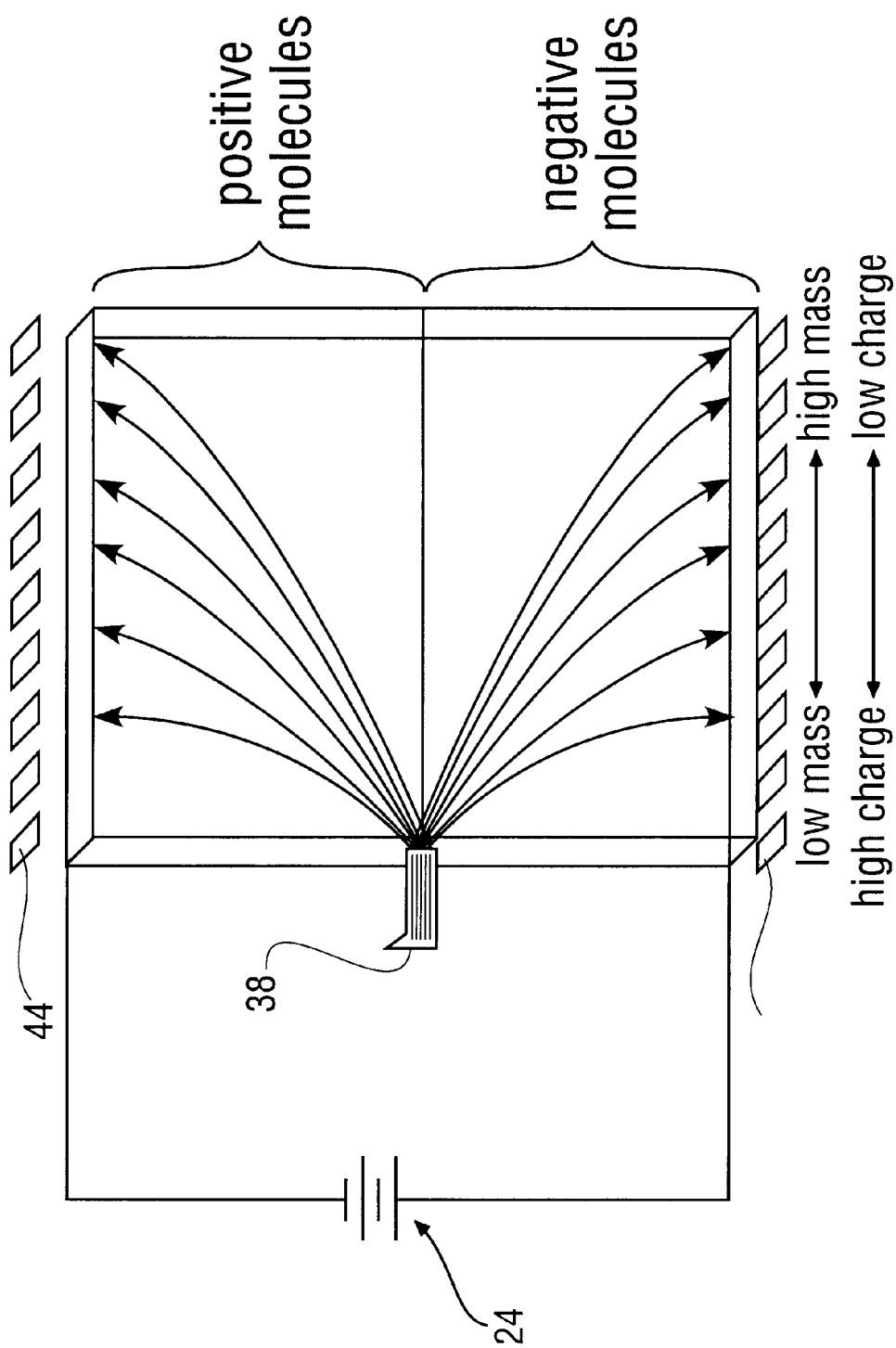
FIG. 6 illustrates classification of a mixture of dissimilar molecules and quantification of molecules by an array of detectors that are placed along the length of the receiving wall or walls.

In a third processing scheme, the mixture is comprised of molecules of both net negative and net positive charge. The third processing scheme is a combination of the first processing scheme and the second processing scheme. To accomplish separation of the entire pool of sample molecules, the apparatus is modified as shown in FIG. 6. Quantification of molecules is performed by an array of detectors 44 that are placed along the length of the receiving wall or walls. Further quantitative and/or qualitiative analysis may be carried out by the formation of a series of depressions along the bottom wall 22 into which substantially discrete packages of classified molecules may be isolated for optional removal and/or in-place analysis.

Various conventional detector methods may be employed for quantifying the number of molecules stuck along the wall, such as capacitance detection, surface-sensitive evanescent wave detection, surface acoustic wave detection, CMOS optical sensors or optical density measurements. A detector type may be chosen depending upon the application.

In another embodiment of the present invention, an inventive classifier is provided that classifies and quantifies charged molecules by field-gradient focusing by using a MEMS classifier. In this embodiment of the invention, a method is provided to introduce 2-dimensional porous media to standard 1-dimensional capillary electrophoresis so that charged molecules such as protein molecules can be separated and quantified for analysis.

In addition to these advantages, this embodiment of the present invention also significantly increases total peak capacity. Increased total peak capacity is a consequence of the comprehensive 2-dimensional nature of the inventive classifier. As described herein, a dynamic equilibrium is established, based on opposing one set of molecular properties in a first direction with a force such as electrical charge, with opposition thereto based on a different set of molecular properties such as size and shape. Hence, the total peak capacity is the product of peak capacities of the individual dimensions.

The classifier described here performs a two-phase operation. The second phase is accomplished by utilizing the apparatus and method described in the previous embodiments.

The first phase of this embodiment of the present invention begins with a conduit that is created with an outlet and inlet on opposing sides. All conduit walls are manufactured of non-conducting material. Three of the walls are impermeable to liquids such as water, whereas one wall is semipermeable as manufactured, for example, in porous silicon. The purpose and function of the semipermeable wall is set forth below.

Figure 7:
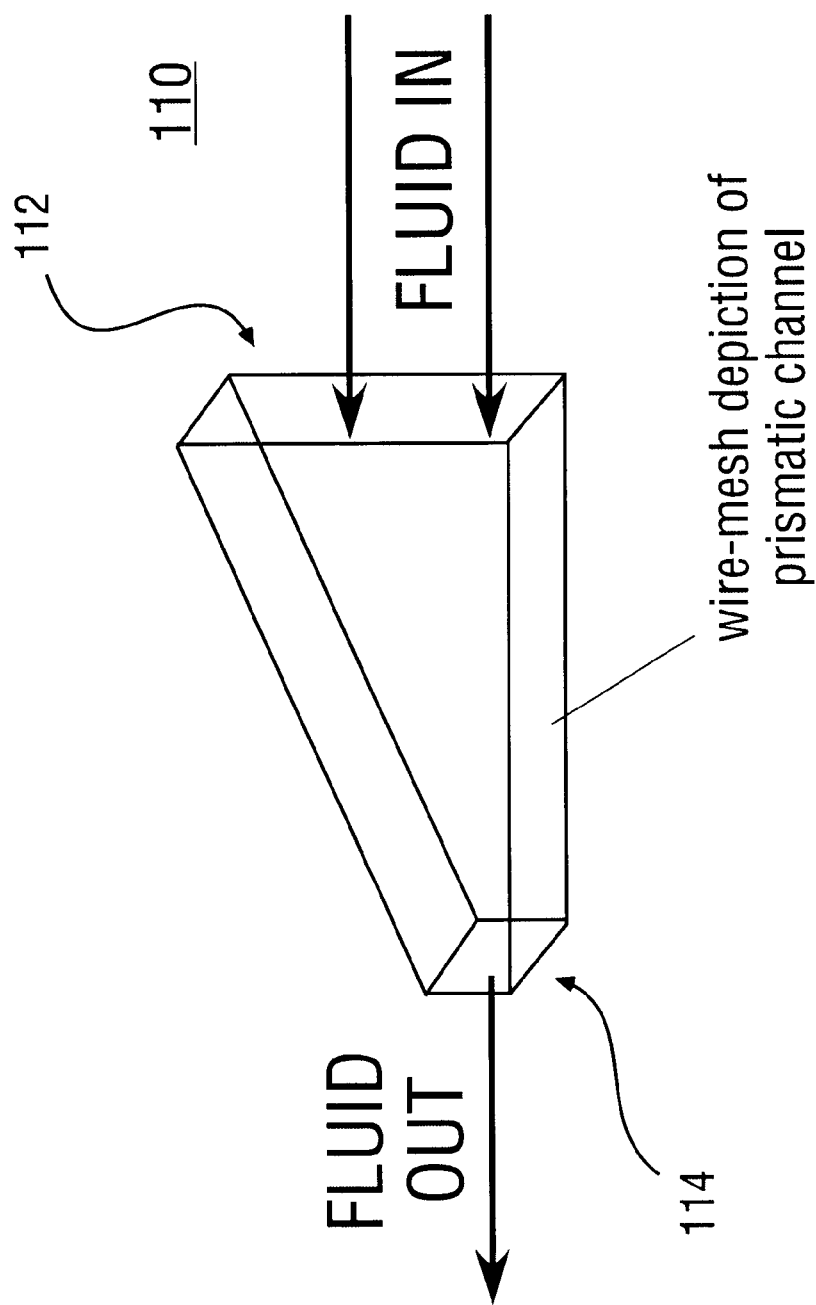
FIG. 7 illustrates a conduit that is a graded structure that is manufactured in the shape of a quadrilateral prism.

The conduit is manufactured in the shape of a quadrilateral prism, which may be referred to as a graded structure. To illustrate this prismatic shape, FIG. 7 provides a view of only the interior of conduit 110. By means of a pump, a homogeneous, isothermal conducting liquid such as water is forced to flow into conduit inlet 112 of conduit 110, and exit at conduit outlet 114. By means of backpressure, conduit 110 is caused to fill completely with liquid.

Figure 8:
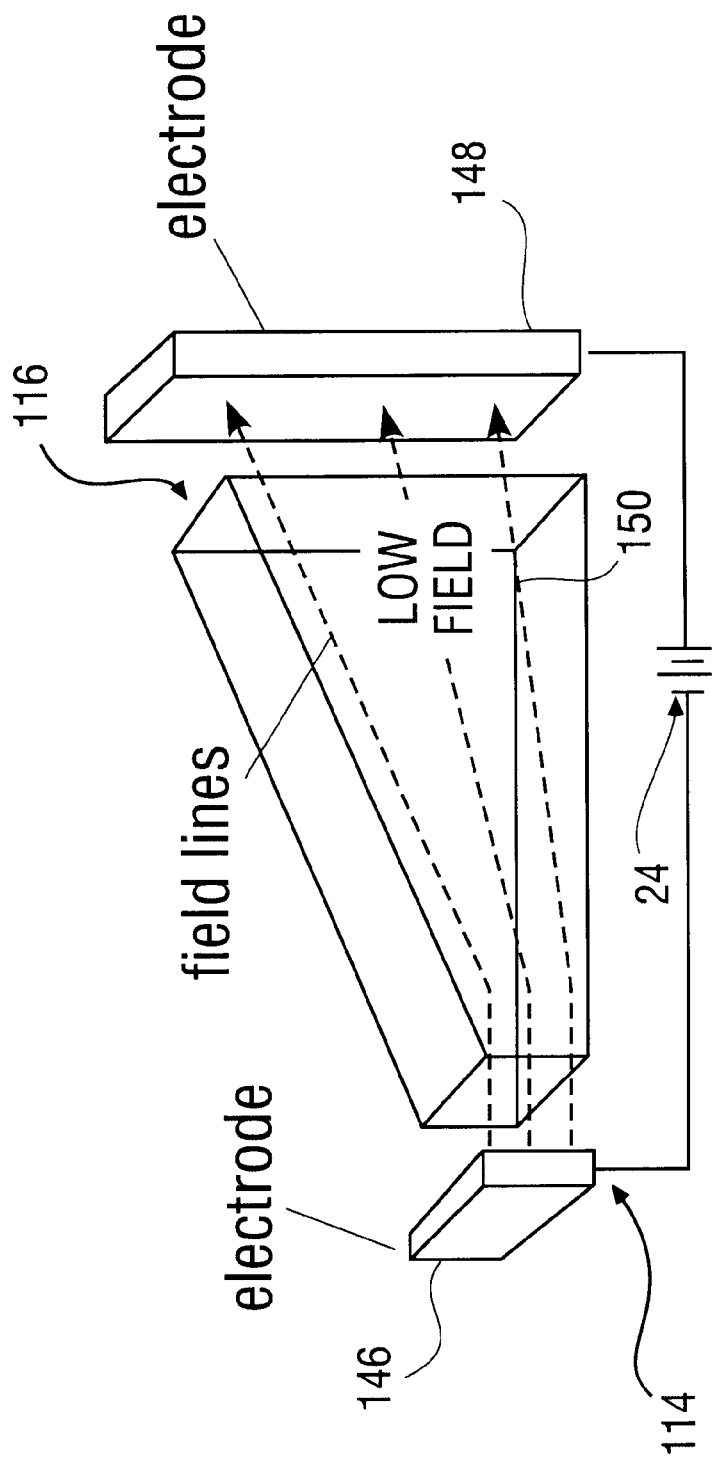
FIG. 8 illustrates electrode placement within the conduit wherein one electrode is placed near the outlet, and another electrode is placed near the inlet of the conduit.

As shown in FIG. 8, a front electrode 146 is placed near conduit outlet 114 without blocking fluid flow, and a back electrode 148 is placed near conduit inlet 112. Since the conduit sidewalls are constructed of electrically non-conducting material and due to disparate electrode sizes, electrical current field lines 150 conform to the prismatic shape of conduit 110. At conduit inlet 112, the electrical current field lines 150 are more dispersed than at conduit outlet 114. Hence, an electric field gradient is established within conduit 110, which in turn exerts an electromotive force on all charged molecules in solution that propels them from one end of conduit 110 to the other. Negatively charged molecules may be propelled along the gradient from high- to low-field, in which case positively charged molecules are propelled from low- to high-field.

Figure 9:
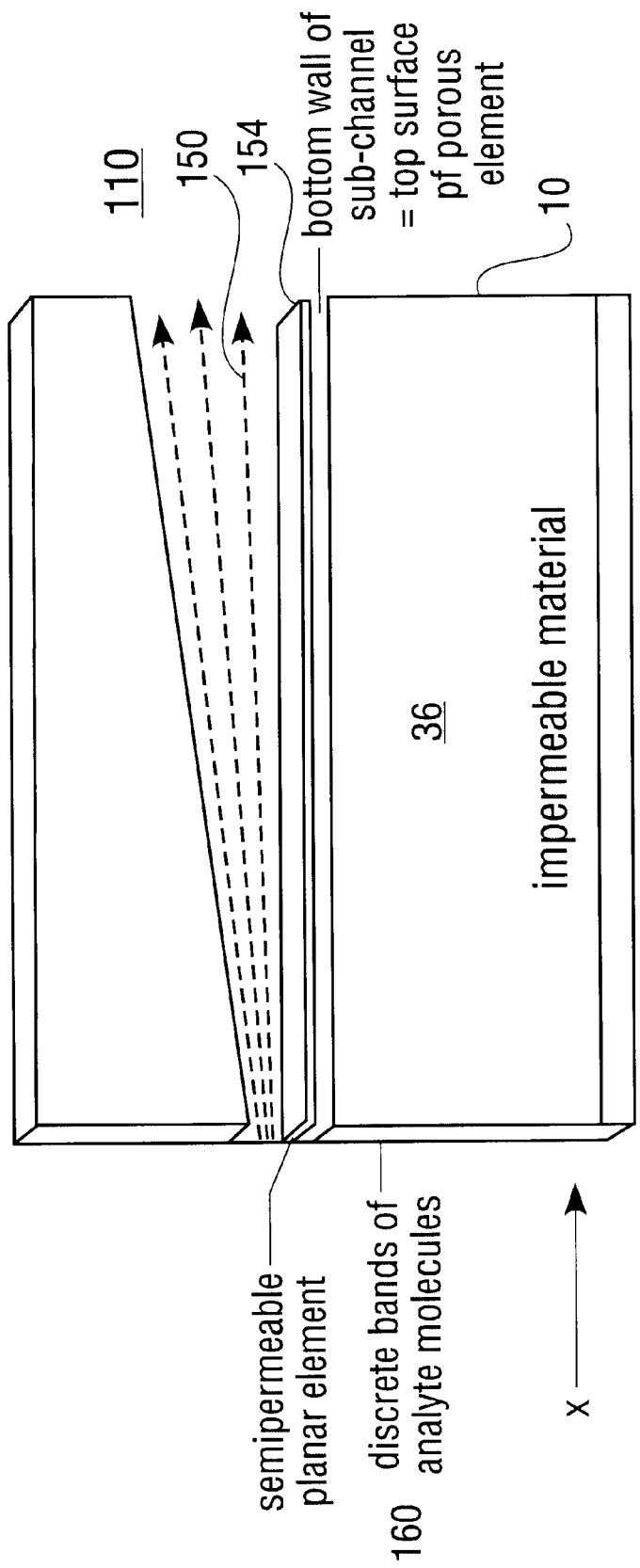
FIG. 9 depicts the prismatic conduit in relation to additional structures.
Figure 10:
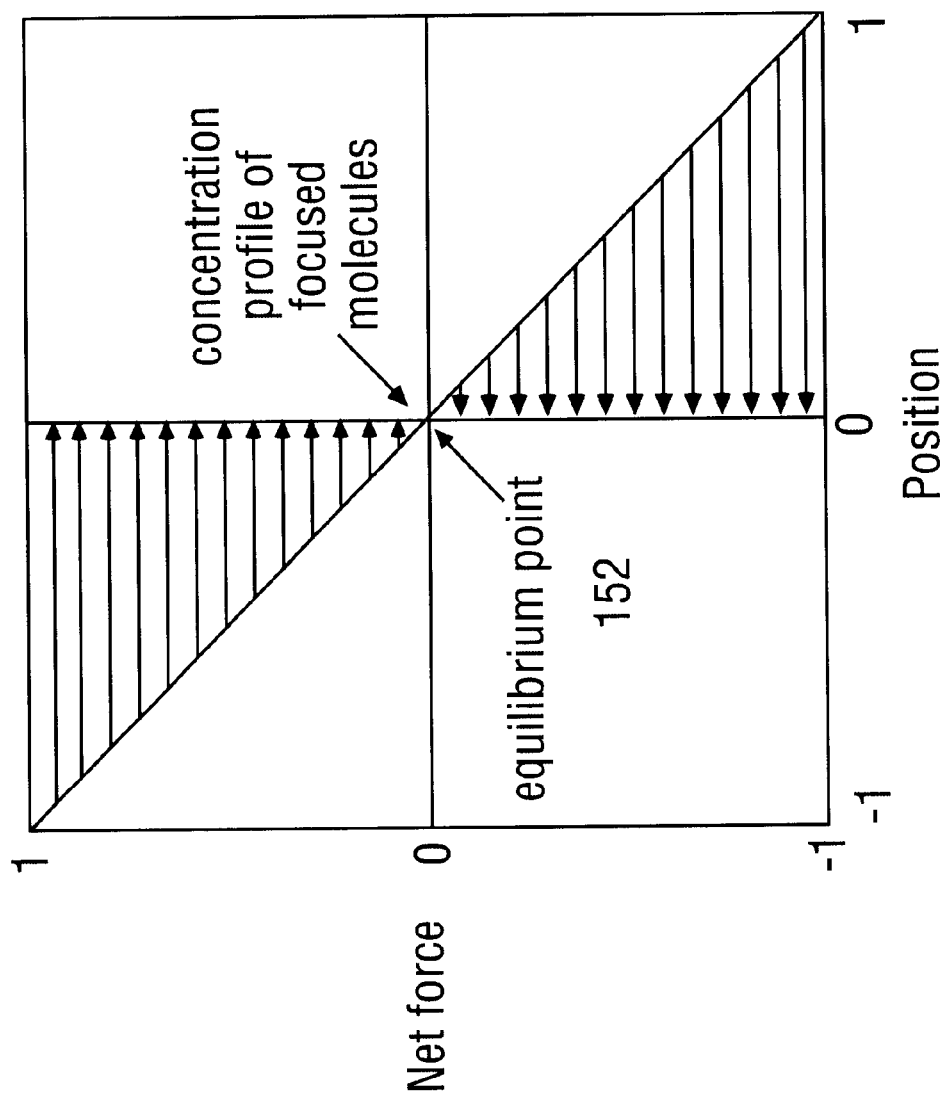
FIG. 10 illustrates how a given molecule will focus at a unique equilibrium position.

FIG. 9 depicts the prismatic conduit 110 in cross-section. FIG. 9 illustrates that charged molecules within conduit 110 simultaneously experience two forces of fluid drag and electrophoresis 150. When these two forces counteract, mixtures of charged molecules in conduit 110 are separated and concentrated or focused at substantially definable positions along conduit 110. The substantially definable position at which any given molecule will focus with other like molecules into discrete or focused bands 160 corresponds to where the two counteracting forces are substantially equal and opposite. Mathematically, this is where the net sum of forces changes direction, as shown graphically in FIG. 10. A given molecule will focus at an equilibrium position, where the net force on the molecule is substantially zero. To the left of this equilibrium position 152, the net force is negative and pushes the molecule rightward toward the equilibrium position 152. Conversely, to the right of equilibrium position 152, the net force is positive and the molecule is pushed leftward, again toward equilibrium position 152.

In this embodiment, the present invention includes three processing schemes that are used to process three different charge states of the molecules to be analyzed. In a first processing scheme, all molecules to be separated are net negative in charge. Referring again to FIG. 9, molecules of negative charge tend to be swept electrophoretically from left to right, in the positive x direction. Hence, separation is achieved if the counteracting fluid flow is imposed in the negative x direction, from right to left.

In the second processing scheme, all molecules to be separated are net positive in charge. The situation is exactly the opposite of the first processing scheme. Molecules of positive charge tend to be swept electrophoretically from right to left, in the negative x direction. Hence, separation is achieved if the counteracting fluid flow is imposed in the positive x direction, from left to right.

In the third processing scheme, the mixture is comprised of molecules of both net negative and net positive charge. If the fluid is caused to flow from right to left, as pictured in FIG. 9, then any molecules carrying a net negative charge will be focused, whereas any molecules carrying a net positive charge will experience two reinforcing forces that sweep them leftward entirely out of conduit 110.

Figure 11:
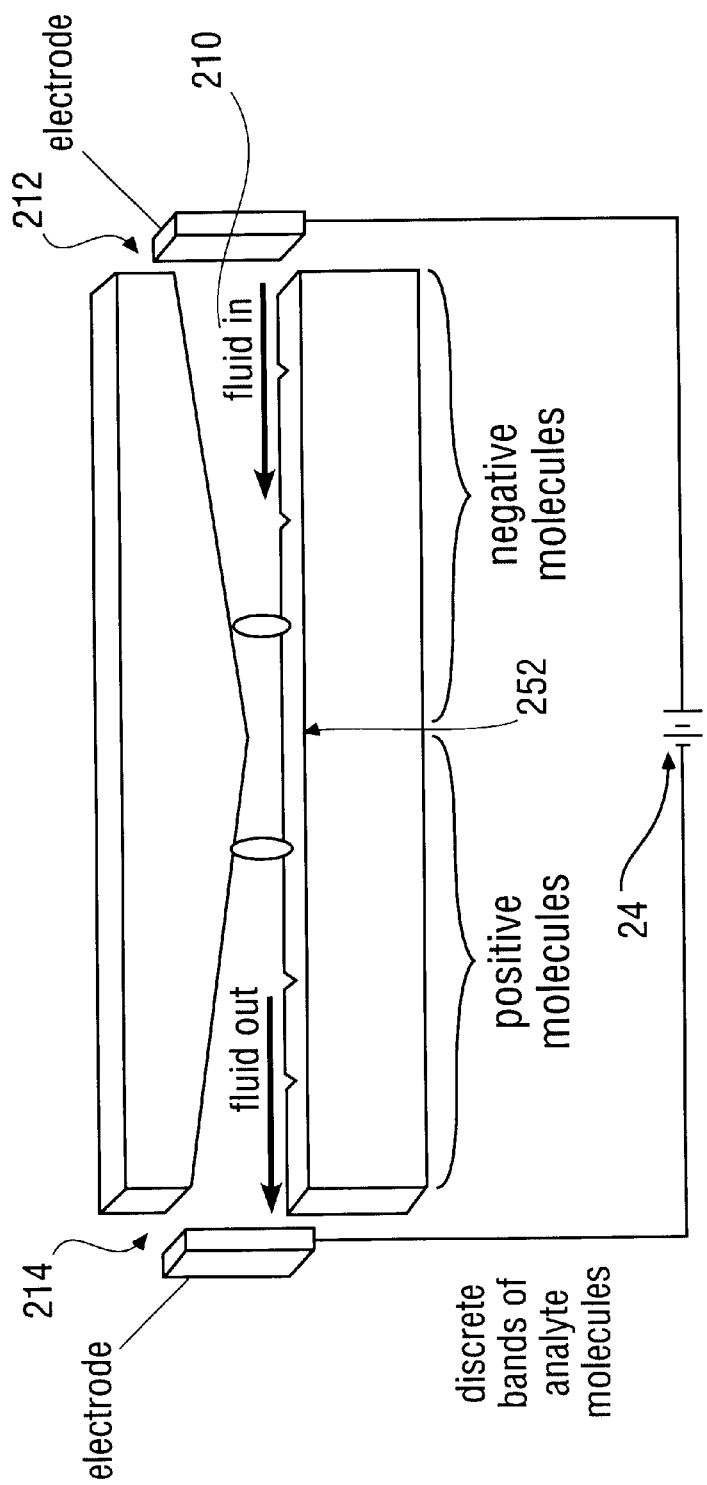
FIG. 11 illustrates a double-prismatic conduit.

In order to simultaneously focus both negative and positive molecules, it is necessary to create the double-prismatic conduit 210 illustrated in FIG. 11.

Given the force vectors of FIG. 9, positive molecules placed at the conduit inlet 212 will experience the additive forces of electrostatics and fluid drag, causing them to move leftward toward the conduit outlet 214. Once swept past the conduit midpoint 252, the electrostatic attraction on the positive molecules will begin to diminish. Eventually, a position will be reached that may be substantially unique to each molecular compound at which the leftward tug of fluid drag substantially balances the rightward tug of moving away from the attractive negative field at the conduit midpoint 252. At this position, a given positive molecule will focus or hold its position in conduit 210.

In contrast, negative molecules placed in conduit inlet 212 will immediately experience the opposed and counteracting forces of electrostatics and fluid. Initially, fluid drag will dominate and cause the negative molecules to be swept toward the repulsive high field at conduit midpoint 252. Eventually, a position will be reached that may be unique to each compound at which the leftward tug of fluid drag substantially balances the rightward repulsive force of a negatively charged molecule approaching a negative electric field. At this position, a given negative molecule will focus.

Figure 12:
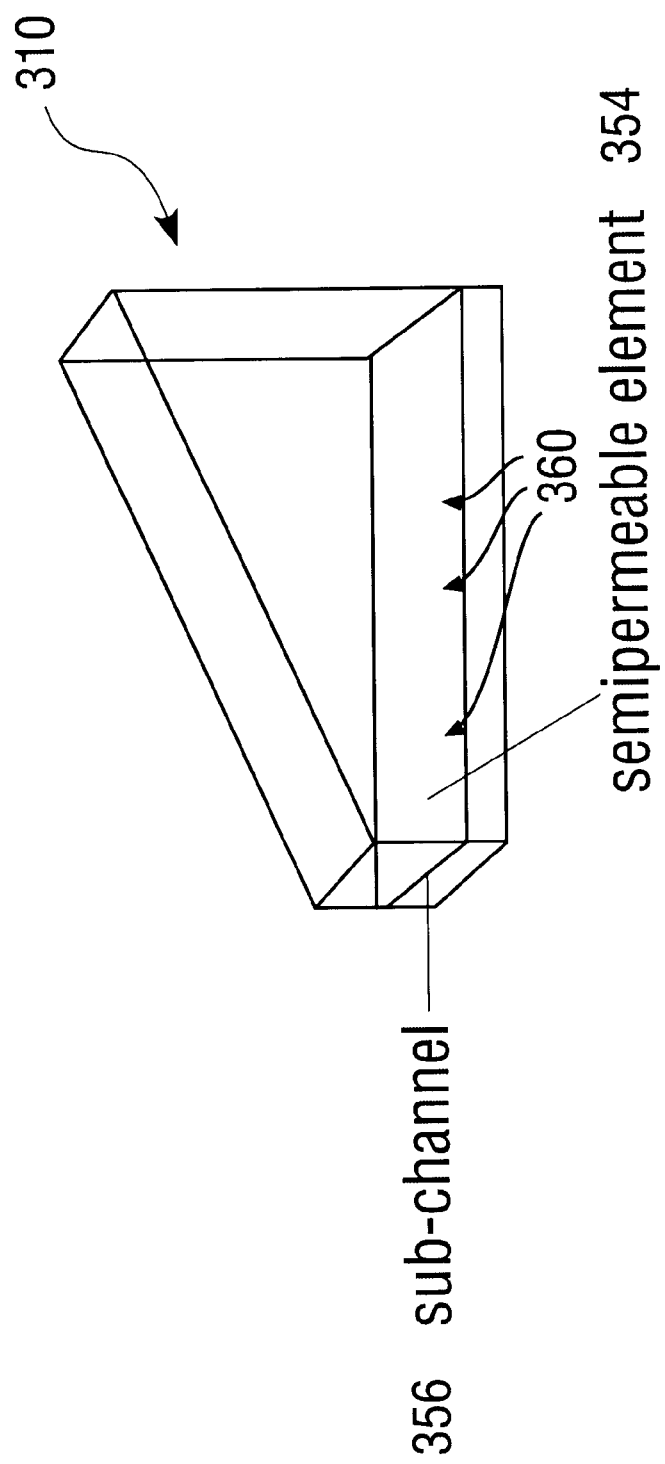
FIG. 12 illustrates a thin, planar, semipermeable element that is co-planar with the bottom wall of the prismatic conduit that creates a sub-channel.

In FIGS. 12–17, only the axisymmetric half of the double-prismatic conduit 210 of FIG. 11 is shown. It is useful to increase the number of components that can be classified within a given process. One strategy is to spatially confine all generated bands of charged molecules. This is accomplished by introducing to the apparatus a thin, planar, semipermeable element 354 that is co-planar with the bottom wall of the prismatic conduit 310, as shown in FIG. 12, thereby creating a sub-channel 356. At the start of the first phase, molecules to be separated are placed inside sub-channel 356.

Figure 13:
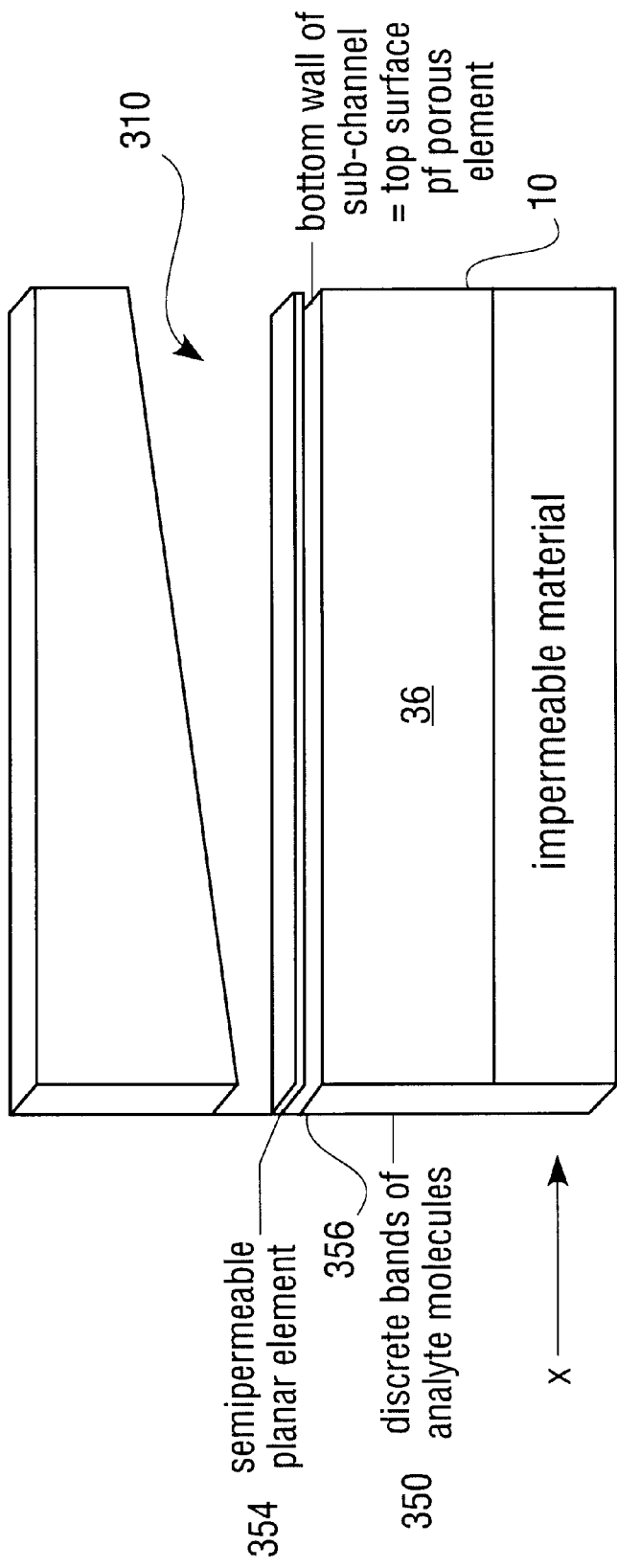
FIG. 13 illustrates focused bands that remain spatially concentrated within the sub-channel.

Semipermeable element 354 is manufactured to be planar and porous with respect to the bulk fluid and electrolytes in conduit 310, but not with respect to the analyte molecules in sub-channel 356. In other words, although a small quantity of analyte may penetrate by diffusion through semipermeable element 354 into conduit 310, the vast majority of analytes will remain in the bulk fluid within sub-channel 356, where they will be subject to the same field gradient and fluid drag as the main conduit 310. During first phase, the focused bands 360 remain spatially concentrated within sub-channel 356, as depicted in FIG. 13. There are other advantages associated with sub-channel 356. In the fluted region 252 of main conduit 210 as seen in FIG. 11, flow rates in main conduit 310 vary as a function of cross-sectional width thereof. However, if semipermeable element 354 is thick enough to prevent bulk fluid flow thereacross, then fluid within sub-channel 356 will flow at a fixed rate. This effect may be of benefit in establishing a uniform slope of change of net force around all equilibrium positions of focused bands 360 of charged molecules, and thereby enhancing the total peak capacity of the inventive classifier.

An alternative approach to establishing the field gradient of the first phase is by an array of wire electrodes within the fluid stream that would have contours symmetrical to electrical current field lines 150 as seen in FIGS. 8 and 9. In this embodiment, each wire may be individually powered to establish a field gradient.

The net charge carried by any given molecule in solution is a function of pH, ionic strength, solution potential, and other solution qualities. Hence, the present invention may require tailoring of solution properties to achieve certain desired separations. Moreover, the classifier may preferably be engineered to ensure that the trajectories of sample molecules do not overshoot the physical dimensions thereof.

As a result of the dynamic equilibrium established in the first phase, the molecules now reside in a sorted state, predominantly by charge. The second phase is to further classify the first classified substances based on size and shape. This is accomplished by utilizing the classifier and method set forth above that separates and quantifies charged molecules by porous media 36 in MEMS structures. Although the inventive method set forth above may sort molecules based simultaneously on charge, size and shape, the molecules at the start of the second phase are already sorted by charge. Hence, no additional sorting by charge may be achieved by the second phase.

In the inventive method set forth above, molecules to be sorted are introduced into the 2-dimensional porous element 36 at a single inlet. In this embodiment, by contrast, the molecules are introduced directly from the positions at which they are focused in the first phase. For example, if a given mixture of molecules is sorted in the first phase into three bands of charged molecules, then each of these three bands constitute the three discrete entry points of sample into semipermeable element 354 separator of the second phase.

Figure 14:
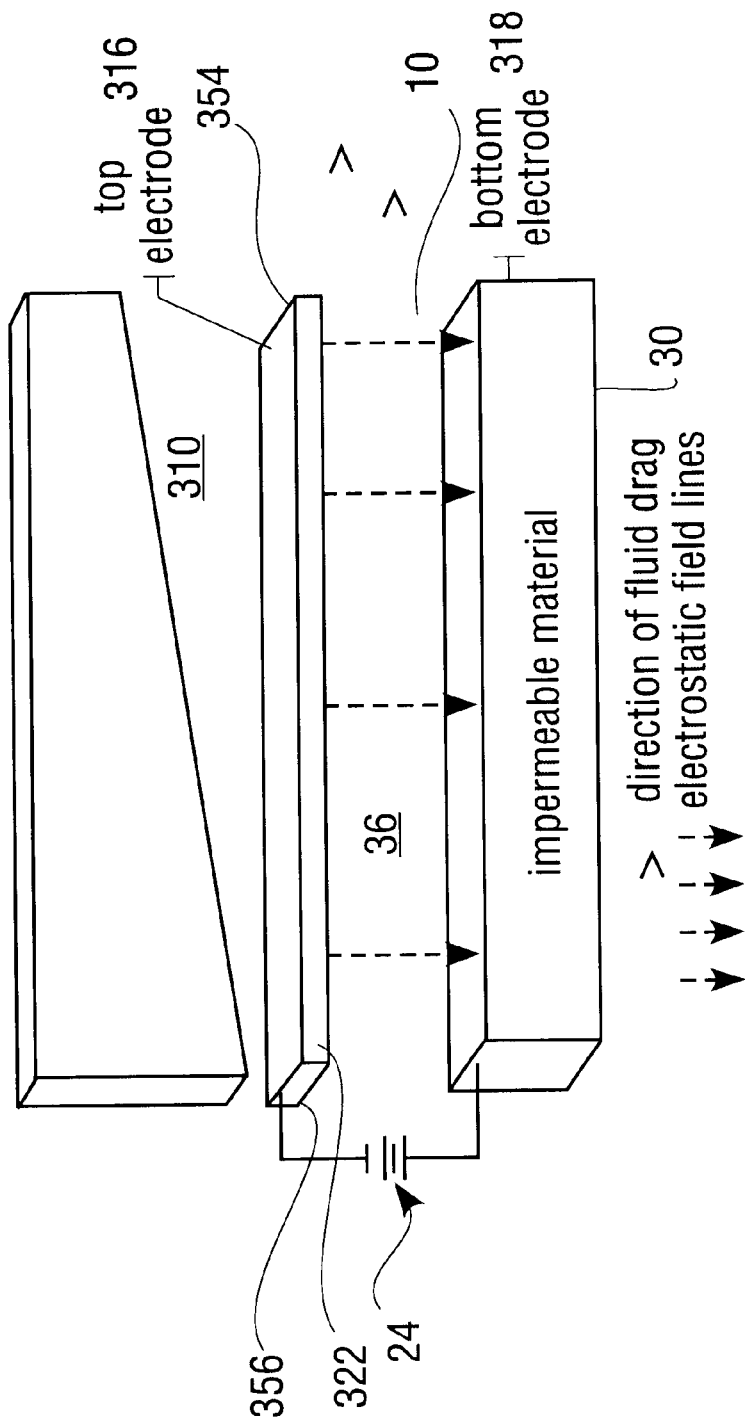
FIG. 14 illustrates an elevational cut-away view of the channel.

To enable the operational coupling of the first phase with a semipermeable element 354 separator in the second phase, a few modifications are made. As illustrated in FIG. 14, the bottom wall 322 of the sub-channel 356 is constituted of one surface of a porous medium 36. Molecules are focused in the immediate vicinity of semipermeable element 354 of the first phase, then directly swept into the porous medium 36 of the second phase for further separation.

Figure 15:
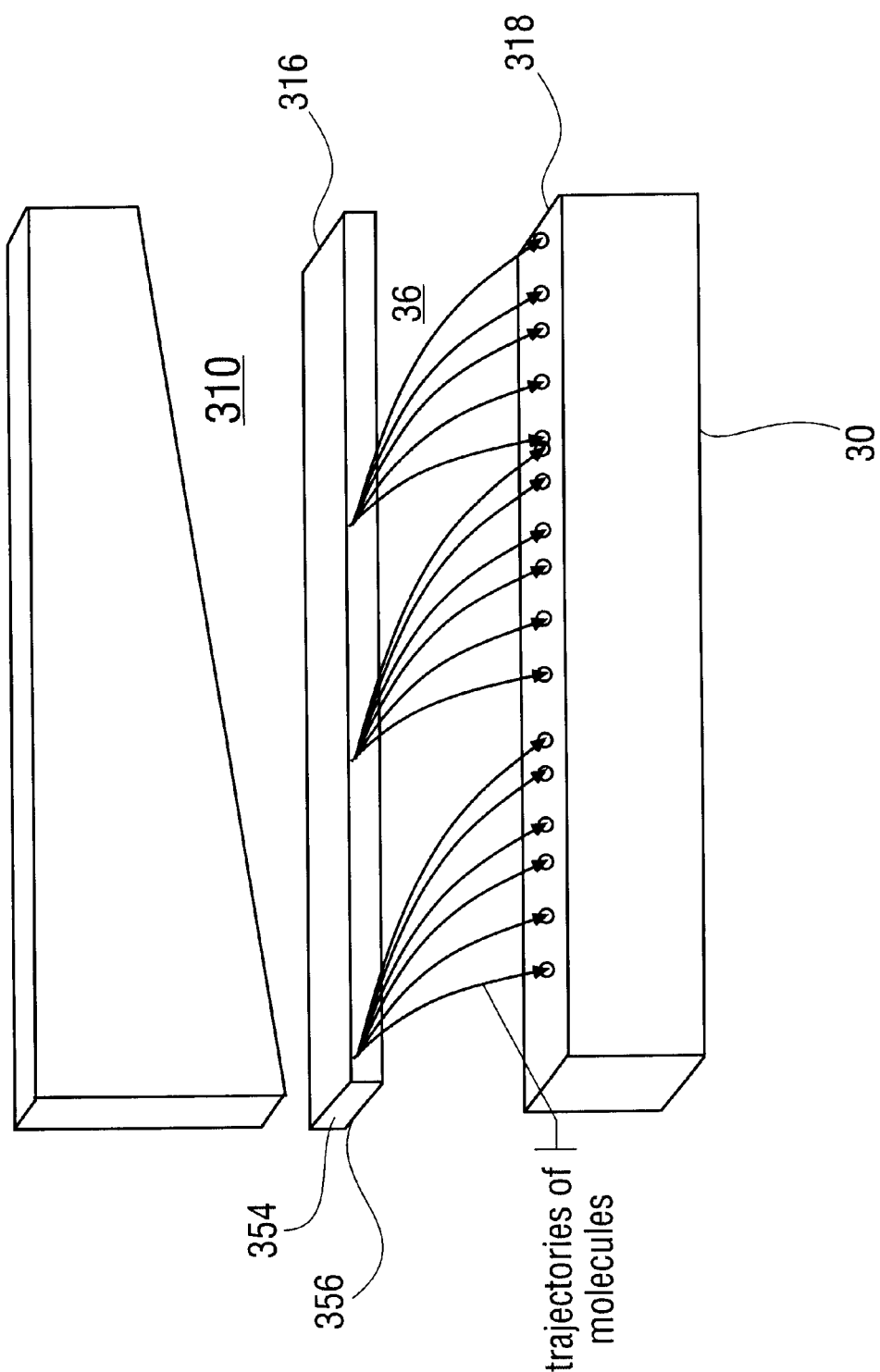
FIG. 15 illustrates further classifying of molecules in the porous medium based on their size and shape.

According to this embodiment of the present invention, once focusing has been completed, the first phase electric field is turned off. Thereafter, a new electric field 362 is established in an orthogonal direction as illustrated in FIG. 14 to cause the first classified substances in their focused bands of charged molecules to move directly to the surface the porous medium 36, and to enter thereinto. Once in porous medium 36, the focused bands of charged molecules are additionally subject to fluid drag, as depicted in FIG. 15.

Figure 16:
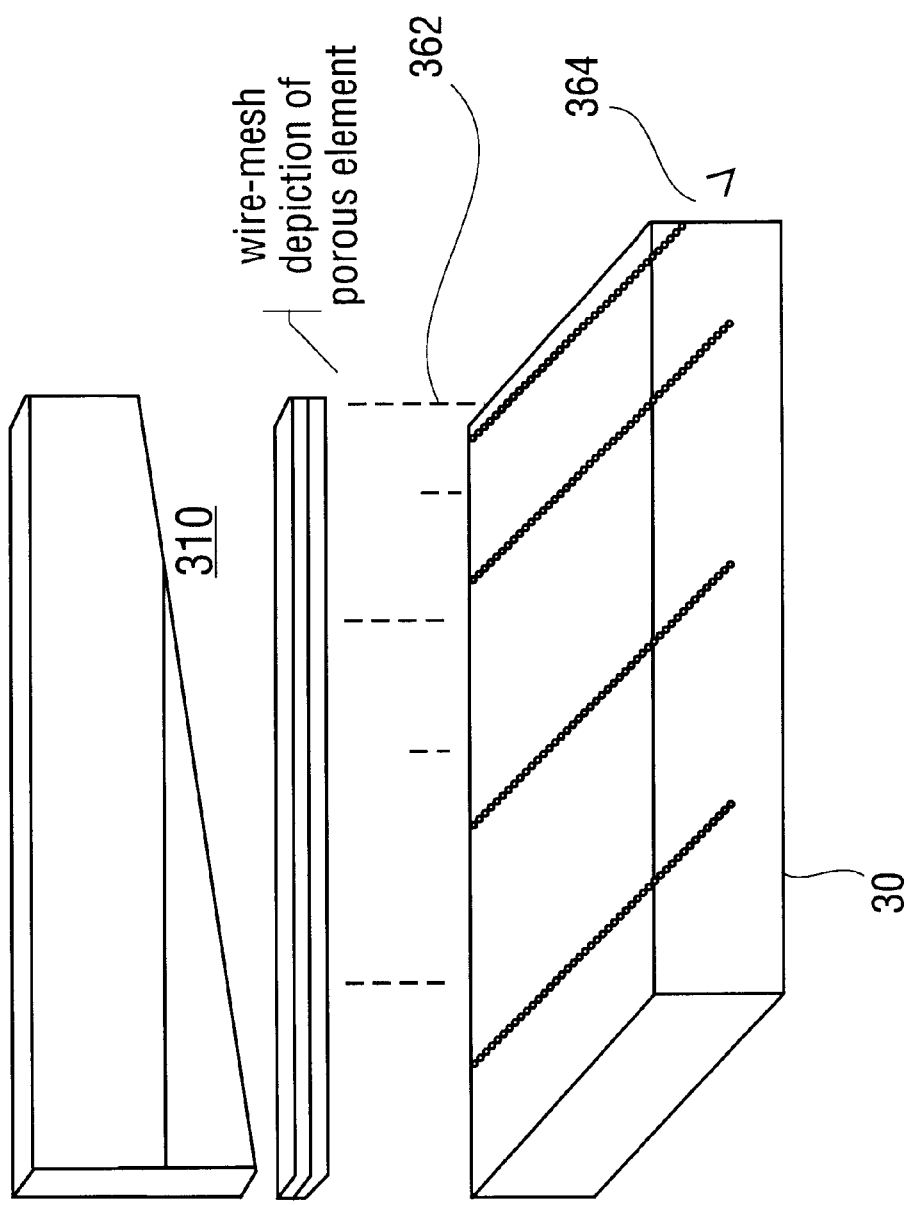
FIG. 16 illustrates expansion of the porous medium in one direction.
Figure 17:
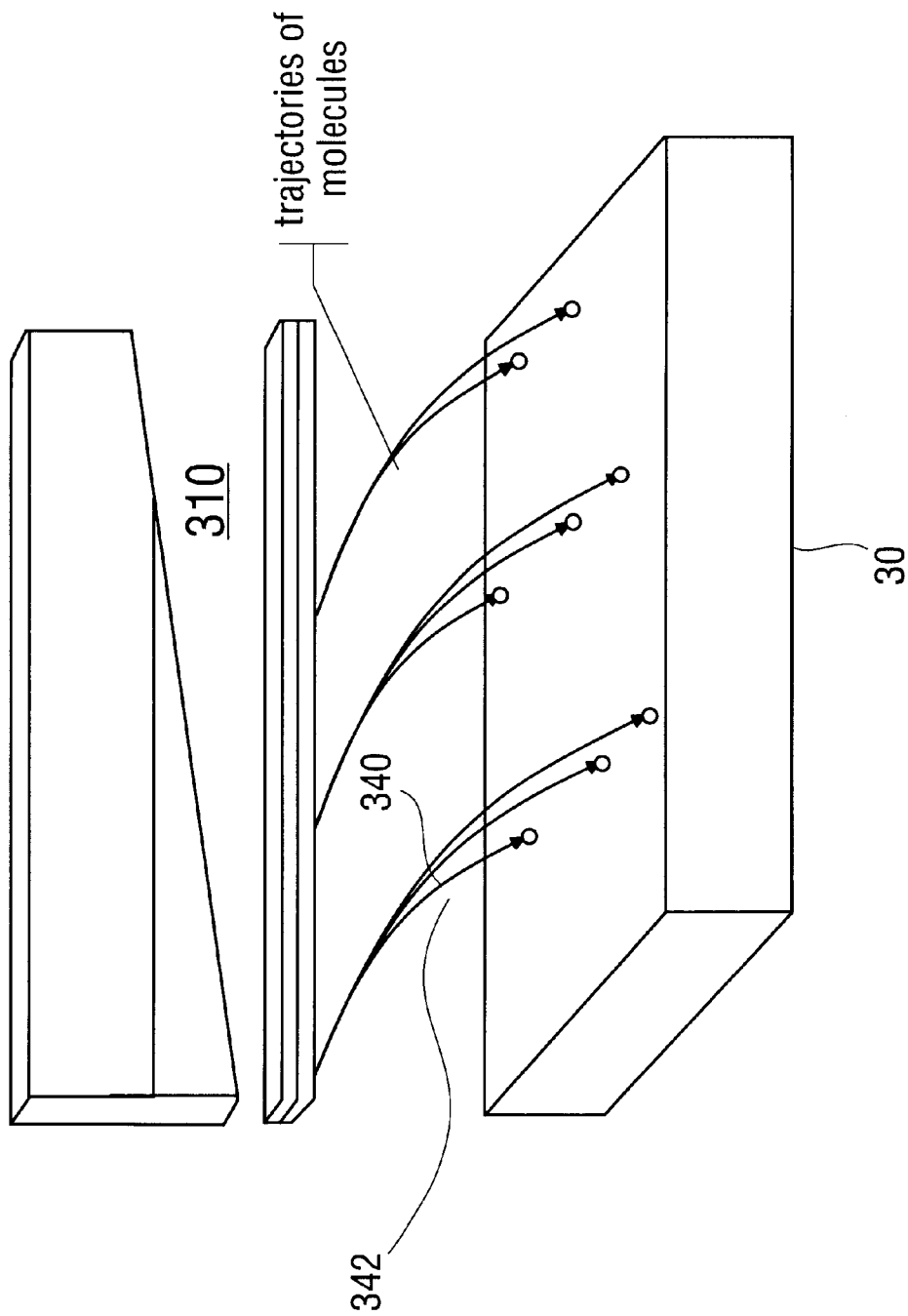
FIG. 17 illustrates negatively charged molecules with transverse trajectories.

The combination of fluid drag and electrophoresis within porous medium 36 results in further sorting of the analyte molecules, based on size and shape, as illustrated in FIG. 16. Final quantification of molecules occurs according to the apparatus and methods described in previous embodiments above.

To establish the new electric field, top electrode 316 and a bottom electrode 318 are situated respectively above and below porous medium 36 top electrode 316, situated within prismatic conduit 310 is constructed in a manner that renders it freely permeable to the free flow of liquid, for example as a solid surface permeated with holes, or as a thin wire or an arrangement of thin wires. During the first phase, top electrode 316 and bottom electrode 318 are electrically neutral in order to avoid altering the field lines imposed during the first phase.

In some circumstances, it is useful to chemically modify the surface state of all molecules in order to impose a single known charge upon the entire population, as for example in the analysis of some protein molecule mixtures. The present invention may use a buffered solution of sodium dodecyl sulfate that is brought into contact with molecules such as proteins at or near the commencement of the second phase. The result is full surface derivitization that may impart a negative charge on all molecules such as proteins as well as a uniform charge/mass ratio.

Field gradient focusing during the first phase may experience some penetration of analyte by diffusion into the semipermeable element 354 within a conduit 310 that is bounded on one side by semipermeable element 354. However, diffusion of the first phase is the only force that may cause analyte to penetrate into conduit 310 through semipermeable element 354. Hence, some slight loss of analyte may occur, but not of appreciable quantity to effect the outcome of the process of the first phase.

As an alternative to this embodiment, at the conclusion of the first phase, focused bands of isolectrically-equivalent molecules are juxtaposed to the surface of porous medium 36 of the second phase. Rather than moving these bands into porous medium 36 by the influence of a second electric field, it is possible, by suitable valving, to redirect the first fluid flow regime of the first fluid flow regime of the bulk fluid and entrained bands to flow into the matrix of porous medium 36. According to the alternate approach, a second set of electrodes is still employed, but turned up to 90 degrees from the previous position described above.

As a second alternative to this embodiment, the porous medium 36 of the second phase is manufactured of sufficient volume to allow comprehensive 2-dimensional chromatography. This is accomplished by expanding porous medium 36 in one direction, as shown in FIG. 16. When the new electric field 362 and fluid flow drag forces 364 are directed as shown in FIG. 16, then negatively charged molecules will exhibit traverse trajectories like those shown in FIG. 17.

Figure 18:
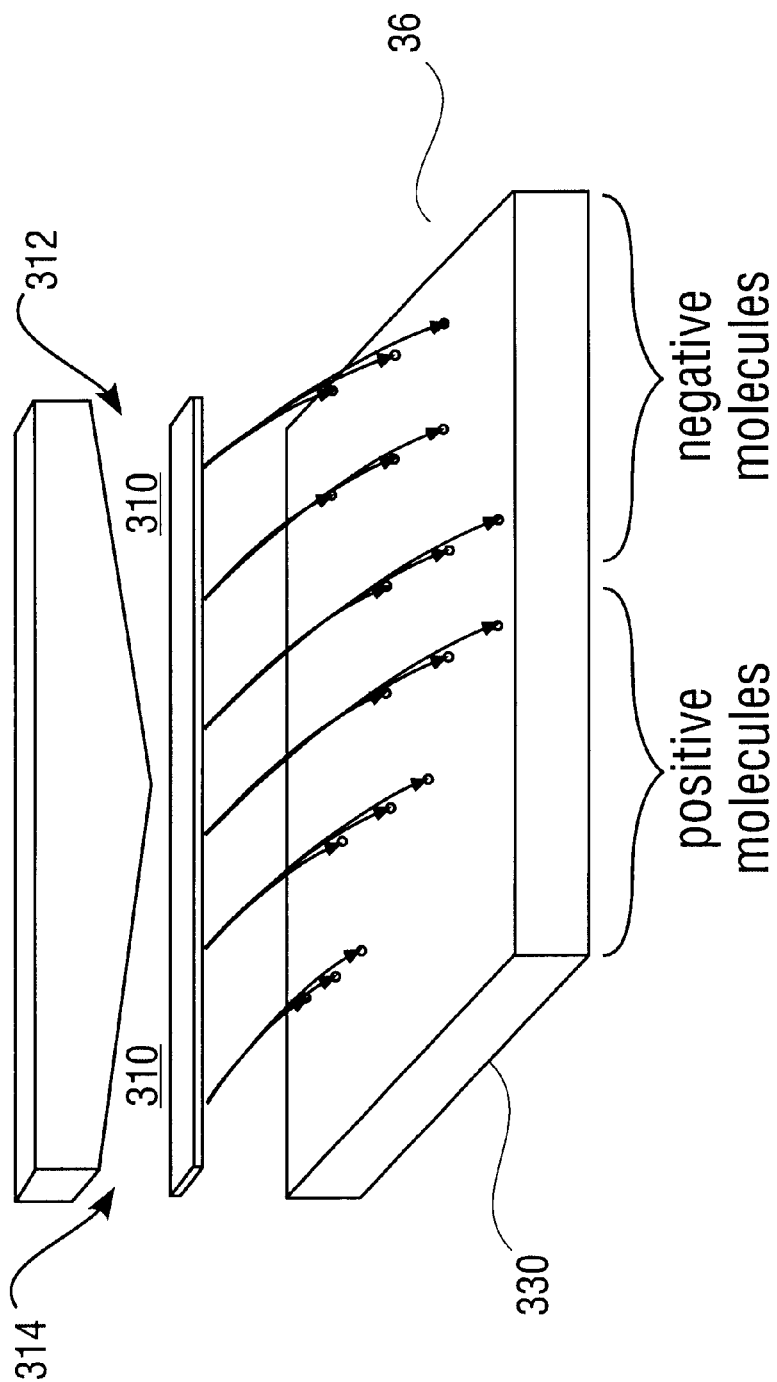
FIG. 18 illustrates a more complete picture of the inventive apparatus, suitable for simultaneous separation of negative and positive molecules.
Figure 19:
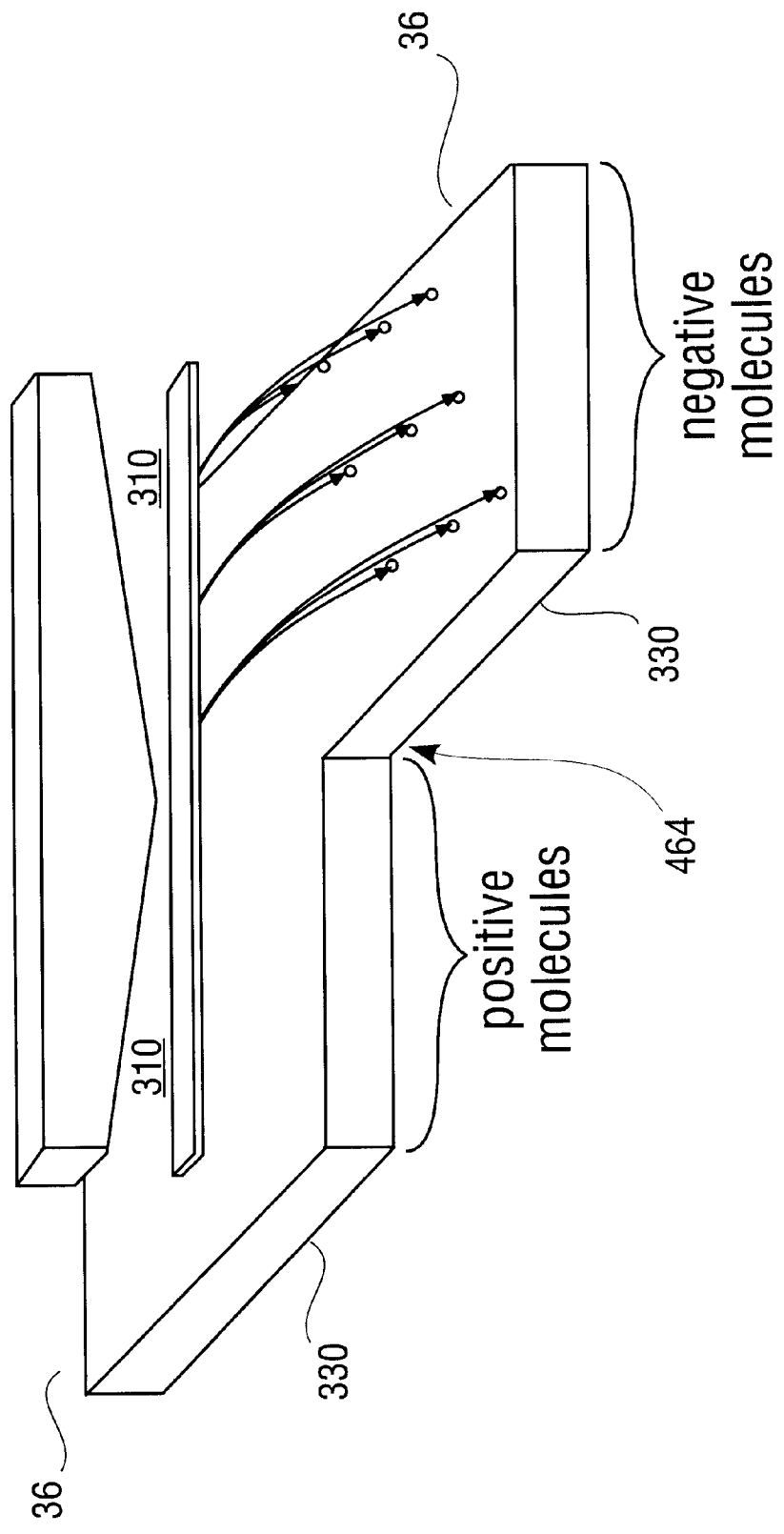
FIG. 19 illustrates an apparatus that adjusts conditions when the polarities of the two electrode pairs are set as appropriate for separation of positive or negative molecules to avoid cross-talk between the two electrode pairs where the vector of one field will be oriented up, and the vector of the other adjacent field will be oriented down.

A complete picture of the classifier, suitable for simultaneous separation of negative and positive molecules, is given in FIG. 18. FIG. 18 illustrates a double prismatic conduit 310 with a conduit inlet 312 and a conduit outlet 314. A porous medium 36 is disposed over a passivation layer 330. However, when the polarities of the two electrode pairs are set as appropriate for classification of molecules bearing a positive or negative charge, there will be substantial cross-talk between the two electrode pairs. Hence, the vector of one field will be oriented up, and the vector of the other adjacent field will be oriented down. To minimize cross-talk, the classifier is modified as shown in FIG. 19 to have a divided channel 464 that contains porous medium 36.

The present embodiment includes two phases that eliminates the complicated, time-consuming and labor-intensive protocol of 2-dimensional polyacrylamide gel electrophoresis, and that eliminates the complicated, capital-intensive and space-intensive method of MALDI mass spectrometry. In addition to these advantages, the present invention also significantly increases total peak capacity. This is a consequence of the comprehensive 2-dimensional nature of the classifier disclosed herein. As described here, a dynamic equilibrium is first established based on one set of molecular properties such as electric charge. Next, there is followed a classification based on a different set of molecular properties such as size and shape. Hence, the total peak capacity is the product of peak capacities of the individual dimensions.

Figure 20:
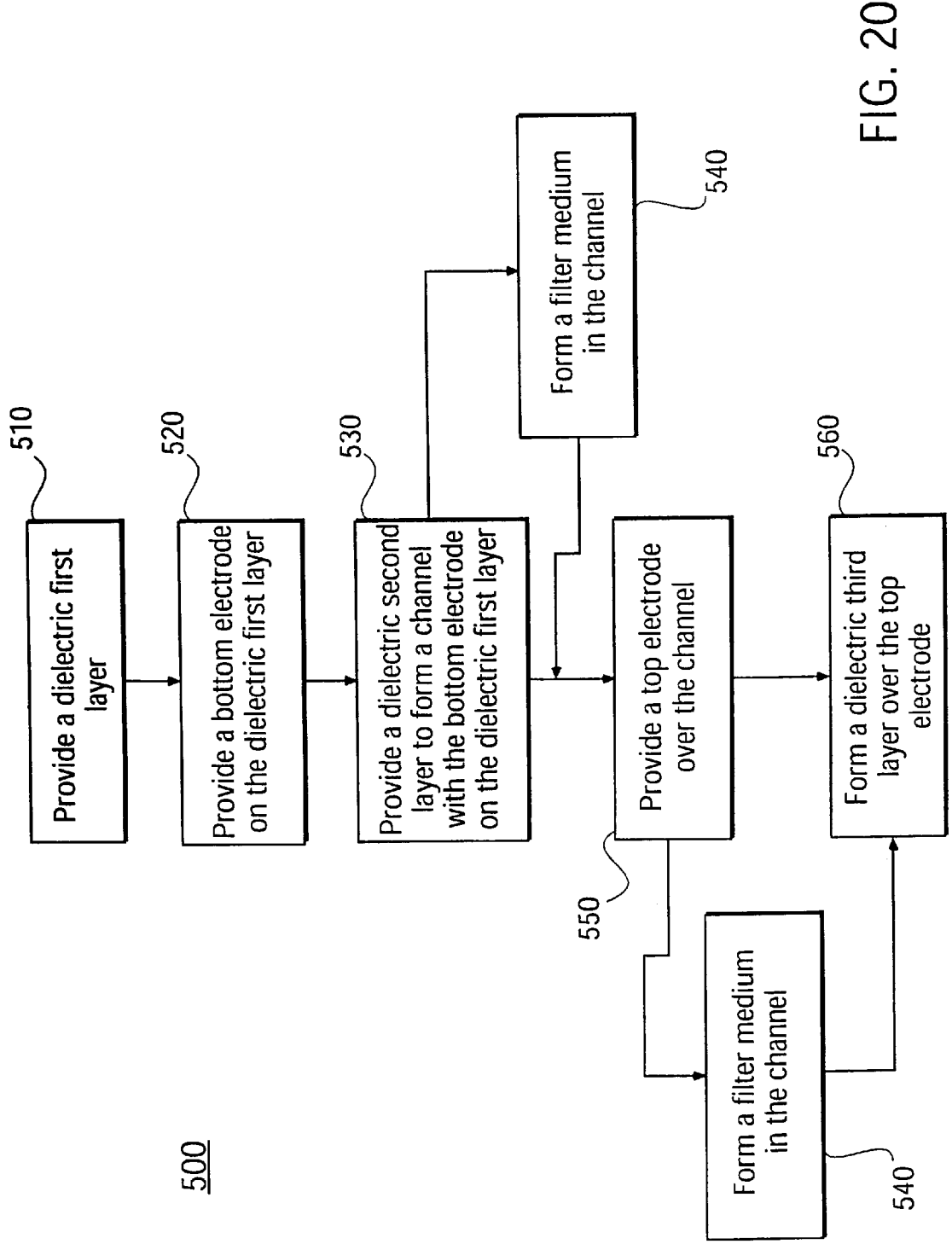
FIG. 20 is a process flow block diagram of the inventive process.

The inventive method of forming a classifier is described in FIG. 20. The method 500 may include providing a dielectric first layer such as bottom wall 22 as illustrated in process flow block 510. Next, a bottom electrode 18 is formed on the dielectric first layer comprising bottom wall 22 as illustrated in process flow block 520. Thereafter, a channel 10 is formed by a second dielectric layer that may comprise sidewalls 34 of channel 10 as illustrated in process flow block 530. A filter medium 36 is formed in channel 10 as illustrated in process flow block 540. A top electrode 16 is formed above filter medium 36 as illustrated in process flow block 550. Additionally, a third dielectric layer that may include passivation layer 28 is formed over the top electrode 16 as illustrated in process flow block 560.

Distinct advantages exist by the present invention. Some advantages regarding the single-phase method of the present invention (referred to herein as the second phase) are set forth below. The utilization of a 2-dimensional porous medium in a MEMS structure as a means of exploiting differential mobility for separating molecules. The utilization of porous silicon in a MEMS structure as the porous medium, or sintered tantalum, or photoresist, etc. The apparatus and method by which electrophoresis is coupled with differential mobility chromatography. The apparatus and method for fixing charged molecules in place along a suitably lengthy electrode. The utilization of an array of detectors placed along the bottom electrode for spatially resolving and quantifying molecules which are fixed in place at or near the electrode surface. The apparatus and method of quantifying the number of molecules fixed on a MEMS surface by capacitance detection, surface-sensitive evanescent wave detection, surface acoustic wave detection, CMOS optical sensors, or optical density measurements. The method of in situ manufacture of porous media in conjunction with conventional lithographic patterning. The apparatus for simultaneous separation of positive and negative molecules.

Some advantages regarding the two-phase embodiment of the present invention are set forth below. The utilization of quadrilateral prism channels, constructed of non-conducting walls and electrodes, to establish electric field gradients in a MEMS structure. The utilization of counteracting force chromatography to isolectrically focus charged molecules in a MEMS structure. The utilization of a semipermeable element to enhance spatial confinement of chromatographically-separated bands in a MEMS structure. The configuration, structure and method that enables the operational coupling of an isolectric focusing apparatus to a molecular mass separating apparatus based on a 2-dimensional porous element. The utilization of electrodes permeated with holes to enable the free flow of fluids into containers of chromatographic separation media in MEMS structures. The utilization of wires as electrodes to enable the free flow of fluids into containers of chromatographic separation media in MEMS structures. The method of surface derivitization to bestow a uniform charge on molecules in MEMS structures. The utilization of valving to redirect the bulk fluid and entrained bands to flow into containers of chromatographic separation media in MEMS structures. The utilization of double-prismatic field gradient channels to accomplish simultaneous isoelectric focusing of positively and negatively charged molecules. The configuration, structure and method of double-prismatic field gradient channels used in conjunction with double-porous-elements to simultaneously separate molecules of both positive and negative charge. The utilization of a 3-dimensional thick porous element to perform differential mobility chromatography in MEMS structures. The configuration, structure and method of a prismatic field gradient channel used in conjunction with a thick porous element to perform integrated isolectric focusing and differential mobility chromatography. The configuration, structure and method of a double-prismatic field gradient channel, used in conjunction with double 3D-porous-elements and double electrode-pairs to perform integrated isolectric focusing and differential mobility chromatography. The configuration to minimize cross-talk between the double electrode-pairs of a double-prismatic field gradient channel, used in conjunction with double 3D-porous-elements.

It will be readily understood to those skilled in the art that various other changes in the details, material, and arrangements of the parts and method stages which have been described and illustrated in order to explain the nature of this invention may be made without departing from the principles and scope of the invention as expressed in the subjoined claims.

What is claimed is:

1. A method of forming a classifier, comprising:
   providing a dielectric first layer;
   forming a bottom electrode on the dielectric first layer, wherein the bottom electrode is selected from a metal and a semiconductor;
   forming a channel to border the bottom electrode, wherein the channel is formed by a second dielectric layer;
   forming a filter medium in the channel, wherein the filter medium comprises porous silicon, silicon granules, dielectric powders, porous organic materials, or metal powders;
   forming a top electrode above the filter medium, wherein the top electrode is selected from a metal and a semiconductor;
   forming a third dielectric layer over the top electrode; and
   forming a detector array in the channel, wherein the detector array comprises a capacitance detector, a surface-sensitive evanescent wave detector, a surface acoustic wave detector, or an optical detector.

2. The method of forming a classifier according to claim 1, further comprising:
   forming a bottom wall on the bottom electrode, wherein the bottom wall comprises a dielectric material.

3. The method of forming a classifier according to claim 1, further comprising:
   forming a top wall over the filter medium, wherein the top wall comprises a dielectric material.

4. The method of forming a classifier according to claim 1, wherein forming a filter medium in the channel comprises in situ formation of porosity in the filter medium.

5. The method of forming a classifier according to claim 1, wherein forming a filter medium in the channel comprises chemical vapor deposition of a filter medium in the channel; and chemical mechanical polishing of the filter medium.

6. The method of forming a classifier according to claim 1, wherein forming a filter medium in the channel comprises forming a porous silicon structure in the channel.

7. The method of forming a classifier according to claim 1, wherein forming a filter medium in the channel comprises forming a sintered metal structure in the channel from metal powder.

8. The method of forming a classifier according to claim 1, wherein forming a filter medium in the channel comprises forming an organic structure in the channel from the organic material.

9. The method of forming a classifier according to claim 1, wherein forming a filter medium in the channel comprises filling the channel with a slurry.

10. The method of forming a classifier according to claim 1, wherein forming a filter medium in the channel comprises in situ formation of porosity in the filter medium.

11. The method of forming a classifier according to claim 1, wherein forming a filter medium in the channel comprises forming a filter medium with an average pore size in a range from about 5 nm to about 10 nm.

12. The method of forming a classifier according to claim 1, wherein the channel forms a quadrilateral prism.

13. A method of classifying a plurality of substances comprising:
    providing a solid state classifier comprising a porous medium disposed between at least two electrodes;
    classifying a plurality of substances by differential mobility chromatography in the porous medium; and
    classifying the plurality of substances by electrophoresis, wherein the plurality of substances is classified along a plurality of positions within the solid state classifier by fixing charged molecules in place along at least one of the at least two electrodes.

14. The method of classifying a plurality of substances according to claim 13, wherein classifying the plurality of substances comprises:
   flowing the plurality of substances in a first direction within the channel; and
   imposing an electromotive force in the channel that acts counter to flowing the plurality of substances.

15. The method of classifying a plurality of substances according to claim 13, wherein classifying the plurality of substances by electrophoresis comprises fixing molecules that bear a positive charge in place along a first of the at least two electrodes, and fixing molecules that bear a negative charge in place along a second of the at least two electrodes.

16. The method of classifying a plurality of substances according to claim 13, wherein classifying the plurality of substances by differential mobility chromatography in the porous medium comprises classifying molecules having a plurality mass ranges.

17. The method of classifying a plurality of substances according to claim 13, further comprising:
   quantifying the plurality of substances by detection thereof with an array of detectors disposed along at least one of the at least two electrodes.

18. The method of classifying a plurality of substances according to claim 13, further comprising:
   quantifying the plurality of substances by detection thereof with an array of detectors disposed along at least one of the at least two electrodes, wherein quantifying comprises capacitance detection, surface-sensitive evanescent wave detection, surface acoustical wave detection, or optical detection.

19. A method of classifying a plurality of substances comprising:
   performing a first classification of substances in a first phase, wherein the first phase configures first classified substances into classification positions by placing a variable electrophoretic field in opposition to a fluid flow regime of the substances;
   passing the first classified substances at their classification positions into a channel that is filled with a porous medium; and
   performing a second classification of the substances in a second phase within the porous medium.

20. The method of classifying a plurality of substances according to claim 19, wherein passing the first classified substances is carried out by redirecting the first fluid flow regime.

21. The method of classifying a plurality of substances according to claim 19, wherein the variable electrophoretic field is formed by a front electrode having a first area and by a back electrode having a second area, wherein the first area and the second area are not equal.

22. The method of classifying a plurality of substances according to claim 19, wherein the variable electrophoretic field is established in a conduit that has a quadrilateral prismatic configuration.

23. The method of classifying a plurality of substances according to claim 19, wherein the variable electrophoretic field is established in a conduit that has a double quadrilateral prismatic configuration.

24. The method of classifying a plurality of substances according to claim 19, wherein performing a second classification of the substances in a second phase comprises: opposing flow of the first classified substances with the porous medium in a second fluid flow regime.

25. The method of classifying a plurality of substances according to claim 19, wherein performing a second classification of the substances in a second phase comprises:
   imposing an electrophoretic field upon the first classified substances in a direction that is nonparallel to flow of the substances in a second fluid flow regime.

26. The method of classifying a plurality of substances according to claim 19, wherein performing a second classification of the substances in a second phase comprises:
   opposing flow of the substances with the porous medium in a second fluid flow regime; and
   imposing an electrophoretic field upon the first classified substances in a direction that is nonparallel to flow of the substances in a second fluid flow regime.

27. The method of classifying a plurality of substances according to claim 19, wherein the first classification of substances in a first phase is carried out in a planar subchannel that is co-planar with a bottom wall of a conduit.

28. The method of classifying a plurality of substances according to claim 19, wherein the first classification of substances in a first phase is carried out in a planar subchannel that is co-planar with a bottom wall of a conduit, wherein passing further comprises:
   passing the first classified substances through a semipermeable element into the channel.

29. The method of classifying a plurality of substances according to claim 19, performing a second classification further comprises:
   turning off the variable electrophoretic field; and
   imposing a constant electrophoretic field upon the first classified substances in a direction that is nonparallel to flow of the substances in a second fluid flow regime.

30. The method of classifying a plurality of substances according to claim 19, further comprising:
   turning off the variable electrophoretic field;
   imposing a constant electrophoretic field upon the first classified substances in a direction that is nonparallel to flow of the substances in a second fluid flow regime, wherein the constant electrophoretic field is imposed by at least two electrodes; and
   quantifying the substances by detection thereof with an array of detectors disposed along at least one of the at least two electrodes, wherein quantifying is carried out by a method comprising capacitance detection, surface-sensitive evanescent wave detection, surface acoustical wave detection, or optical detection.

31. The method of classifying a plurality of substances according to claim 19, wherein performing a second classification further comprises:
   dividing the channel into first and second portions, wherein the porous medium is disposed in the divided channel, and wherein at least one substance that bears a positive charge is second classified in the first portion and wherein at least one substance that bears a negative charge is second classified in the second portion.

32. A classifier comprising:
   a first dielectric layer;
   a bottom electrode disposed substantially parallel planar to the first dielectric layer;
   a top electrode spaced apart from and disposed substantially parallel planar to the bottom electrode;
   a porous medium disposed between the top electrode and the bottom electrode, wherein the porous medium is divided into a positive-charge substance section and a negative-charge substance section; and a second dielectric layer that forms a channel for the porous medium.

33. The classifier according to claim 32, further comprising:

a conduit disposed above the top electrode, wherein the conduit comprises an inlet end and an outlet end;

a front electrode disposed at the inlet end of the conduit and having a first area;

a back electrode disposed at the outlet end of the conduit having a second area; and a sub-channel, wherein the sub-channel is disposed between the conduit and the porous medium.

34. The classifier according to claim 33, wherein the conduit comprises a quadrilateral prism.

35. The classifier according to claim 33, wherein the conduit comprises a double quadrilateral prism.

* * * * *